United States Patent
Wright et al.

(10) Patent No.: US 9,765,064 B1
(45) Date of Patent: Sep. 19, 2017

(54) ALPHA-HYDROXY-BETA-AZIDO-TETRAZOLES

(71) Applicants: CENTRE NATIONAL DE LA RECHERCHE SCIENTIFIQUE, Paris (FR); UNIVERSITE VERSAILLES SAINT-QUENTIN-EN-YVELINES, Versailles (FR)

(72) Inventors: Karen Wright, Saint-Cloud (FR); Francois Couty, Malakoff (FR); Pierre Quinodoz, Saint-Julien-en-Genevois (FR); Bruno Drouillat, Saint-Cloud (FR)

(73) Assignees: CENTRE NATIONAL DE LA RECHERCHE SCIENTIFIQUE, Paris (FR); UNIVERSITE VERSAILLES SAINT-QUENTIN-EN-YVELINES, Versailles (FR)

( * ) Notice: Subject to any disclaimer, the term of this patent is extended or adjusted under 35 U.S.C. 154(b) by 0 days.

(21) Appl. No.: 15/067,865

(22) Filed: Mar. 11, 2016

(51) Int. Cl.
| | |
|---|---|
| *C07D 257/04* | (2006.01) |
| *C07D 403/08* | (2006.01) |
| *C07D 403/14* | (2006.01) |
| *C07D 409/06* | (2006.01) |

(52) U.S. Cl.
CPC ......... *C07D 409/06* (2013.01); *C07D 257/04* (2013.01); *C07D 403/08* (2013.01); *C07D 403/14* (2013.01)

(58) Field of Classification Search
None
See application file for complete search history.

(56) References Cited

PUBLICATIONS

Angelo, N. G. et al., "Nonpeptidic Foldamers from Amino Acids: Synthesis and Characterization of 1,3-Substituted Triazole Oligomers", Journal of the American Chemical Society, 2005, New York, NY 10003, vol. 127, No. 49, pp. 17134-17135.

Meldal, M. et al., "Cu-Catalyzed Azide—Alkyne Cycloaddition", Chemical Reviews, 2008, Vaby, Denmark, vol. 108, pp. 2952-3015.

Wittenberger, S.J. et al., "Dialkyltin Oxide Mediated Addition of Trimethylsilyl Azide to Nitriles. A Novel Preparation of 5-Substituted Tetrazoles", Journal of Organic Chemistry, 1993, Abbot Park, Illinois, USA, vol. 58, pp. 4139-4141.

Wardrop, D. J. et al., "Dehydrative Fragmentation of 5-Hydroxyalkyl-1H-tetrazoles: A Mild Route to Alkylidenecarbenes", Organic Letters, 2012, Chicago, Ilinois, USA, vol. 14, No. 6, pp. 1548-1551.

Quinodoz, P. et al., "Regio- and stereoselective synthesis of α-hydroxy-β-azido tetrazoles", Organic Chemistry Frontiers, 2015, vol. 2, pp. 492-496.

Sharma, S. et al., "Synthesis of novel 3, 5-disubstituted-dihydroisoxazoles from methyl undec-10-enoate and soxazoles, triazole and tetrazolo-triazole from methyl undec-10-ynoate," Chinese Chemical Letters, Elsevier Ltd, GB, vol. 20, No. 10, Oct. 2009, pp. 1145-1149.

*Primary Examiner* — Alicia L Otton
(74) *Attorney, Agent, or Firm* — Young & Thompson

(57) ABSTRACT

Alpha-hydroxy-beta-azido tetrazole compounds of formula (I):

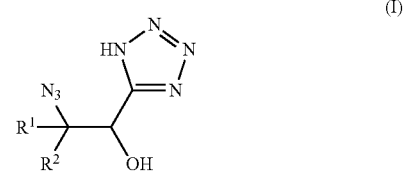

a process for manufacturing alpha-hydroxy-beta-azido tetrazoles of formula (I), and their use for synthesizing new compounds, e.g. in "click" chemistry.

20 Claims, No Drawings

ALPHA-HYDROXY-BETA-AZIDO-TETRAZOLES

FIELD OF INVENTION

The present invention pertains to chemistry, especially to organic chemistry and to the synthesis of organic compounds.

The present invention relates to alpha, beta-substituted tetrazole compounds, especially alpha-hydroxy-beta-azido-tetrazole compounds, and their manufacturing process. The present invention further relates to the use of alpha-hydroxy-beta-azido-tetrazoles for synthesizing new compounds, especially but not limitatively in "click" chemistry.

BACKGROUND OF INVENTION

Tetrazoles have found applications in various domains including material science, energetic materials, coordination chemistry, organic synthesis, and especially medicinal chemistry, due to the fact that 5-substituted tetrazoles (5-ST) are bioisosteres of carboxylic acids. Therefore, there is a need of novel methods for introducing a tetrazole functional group in compounds, e.g. in organic molecules.

The 1,3-dipolar cycloaddition (Huisgen reaction) of azides and alkynes leads to 5-membered triazole heterocycles and has gained considerable interest in the field of organic synthesis since the development of copper (I)-catalysed procedures by Medal and Tornøe. Copper-catalysed azide-alkyne cycloaddition (CuAAC) is a well-known "click" reaction, which is very general and has many attractive features, including: high or quantitative yields, robustness, insensibility, orthogonality, and compatibly with biological and polymerization conditions (Meldal, M. and Tomoe, C. W., Chemical Reviews 2008, Vol. 108, pp. 2952-3015.). A particularly advantageous aspect of CuAAC is that it allows orthogonal ligation reactions, which means that a dedicated set of reaction conditions will lead to a ligation reaction occurring specifically on a functional group of a molecule, without affecting the others.

Due to the popularity of CuAAC reaction, many libraries of compatible azides and alkynes are available. However, there is a need from improvement of the selectivity of CuAAC reactions and/or reduction of the number of steps for the synthesis of complex molecules. Therefore, there is still a need for novel reactants having specific features advantageous for CuAAC and presenting a variety of reactive groups, especially tetrazoles groups. There is also a need for reactants comprising "latent" or "hidden" functional groups, i.e. groups which will not react in CuAAC conditions, but may be easily converted to azide or alkyne when another reactive group is required, thus allowing sequential CuAAC reactions.

The applicant surprisingly established that alpha-hydroxy-beta-azido-tetrazoles could be useful molecular scaffolds for chemical synthesis, in particular for sequenced synthesis. Therefore, the applicant conceived and successfully reduced to practice the manufacture of alpha-hydroxy-beta-azido-tetrazoles and their use as reactant, especially in "click" reactions.

SUMMARY

In a first aspect, the invention relates to an alpha-hydroxy-beta-azido tetrazole compound of formula (I):

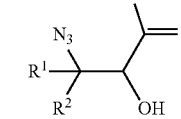

wherein $R^1$ and $R^2$ are each independently hydrogen, hydrocarbyl, aryl, heteroaryl, hydrocarbylaryl, arylhydrocarbyl, hydrocarbylheteroaryl, or heteroarylhydrocarbyl groups; or $R^1$ and $R^2$ form together a group being hydrocarbyl, aryl, heteroaryl, hydrocarbylaryl, arylhydrocarbyl, hydrocarbylheteroaryl or heteroarylhydrocarbyl;

wherein the group is optionally substituted by at least one hydrocarbyl, heteroaryl, oxo, hydroxyl, amido, amino, nitro, carboxylo, formyl, halo, thioxo or sulfhydryl;

wherein the group is optionally interrupted or terminated by at least one group being —O—; —S—; or —NR$^N$— wherein R$^N$ is hydrogen, hydrocarbyl, aryl, or a combination thereof; and wherein the nitrogen or sulfur atoms substituting or comprised in the group are optionally oxidized;

and stereoisomers thereof; and salts thereof; and solvates thereof.

According to an embodiment, $R^1$ and $R^2$ are each independently selected from the group consisting of hydrogen, alkyl, alkenyl, aryl, heteroaryl, alkylaryl, arylalkyl, alkenylaryl, and arylalkenyl groups; wherein the groups are optionally substituted by at least one group selected from the group consisting of hydroxyl, alkyl, alkenyl, aryl, alkylaryl, arylalkyl, amino, nitro, halo and sulfhydryl; and wherein the groups are optionally interrupted or terminated by at least one group selected from the group consisting of —O—; —S—; and —NR$^N$— wherein R$^N$ is selected from the group consisting of hydrogen, alkyl, alkenyl, aryl, and a combination thereof.

According to an embodiment, $R^1$ and $R^2$ are each independently selected from the group consisting of hydrogen, alkyl, alkenyl, aryl, heteroaryl, alkylaryl and alkenylaryl groups; wherein the groups are optionally substituted by at least one group selected from the group consisting of hydroxyl, alkyl, amino, nitro, halo and sulfhydryl; and wherein the groups are optionally interrupted or terminated by at least one group selected from the group consisting of —O—; —S—; and —NR$^N$— wherein R$^N$ is selected from the group consisting of hydrogen, alkyl, alkenyl, aryl, alkylaryl, and arylalkyl.

According to an embodiment, $R^1$ and $R^2$ are each independently selected from the group consisting of hydrogen, alkyl, aryl and alkenylaryl groups; and the groups are optionally substituted by at least one halo group.

According to an embodiment, $R^1$ and $R^2$ form together a group selected from the group consisting of alkyl, alkenyl, aryl, alkylaryl, arylalkyl, alkenylaryl and arylalkenyl; wherein the group is optionally substituted by at least one group selected from the group consisting of hydroxyl, alkyl, alkenyl, aryl, alkylaryl, arylalkyl, amino, nitro, halo and sulfhydryl; and wherein the group is optionally interrupted or terminated by at least one group selected from the group consisting of —O—; —S—; and —NR$^N$— wherein R$^N$ is selected from the group consisting of hydrogen, alkyl, alkenyl, aryl, and a combination thereof.

According to an embodiment, $R^1$ and $R^2$ form together a group selected from the group consisting of alkyl, alkylaryl and arylalkyl; wherein the group is optionally substituted by at least one group selected from the group consisting of hydroxyl, alkyl, amino, nitro and halo; and wherein the group is optionally interrupted or terminated by at least one group selected from the group consisting of —O— and —NR$^N$— wherein R$^N$ is selected from the group consisting of hydrogen, alkyl, alkenyl, aryl, alkylaryl, and arylalkyl.

According to an embodiment, R$^1$ and R$^2$ form together a group selected from the group consisting of alkyl and aryl.

According to an embodiment, the alpha-hydroxy-beta-azido-tetrazole is selected from the group consisting of: 2-azido-2-phenyl-1-(1H-tetrazol-5-yl)ethan-1-ol; 2-azido-2-(naphthalen-2-yl)-1-(1H-tetrazol-5-yl)ethan-1-ol; 2-azido-2-(4-chlorophenyl)-1-(1H-tetrazol-5-yl)ethan-1-ol; 2-azido-1-(1H-tetrazol-5-yl)-2-(thiophen-2-yl)ethan-1-ol; 2-azido-4-phenyl-1-(1H-tetrazol-5-yl)but-3-en-1-ol; 2-azido-1-(1H-tetrazol-5-yl)nonan-1-ol; 2-azido-2-ethyl-1-(1H-tetrazol-5-yl)butan-1-ol; and 2-azido-2,2-diphenyl-1-(1H-tetrazol-5-yl)ethan-1-ol; (1-azidocyclopentyl)(1H-tetrazol-5-yl)methanol; (1-azidocyclohexyl)(1H-tetrazol-5-yl)methanol; (1-azidocycloheptyl)(1H-tetrazol-5-yl)methanol; (1-azidocyclooctyl)(1H-tetrazol-5-yl)methanol; or (9-azido-9H-fluoren-9-yl)(1H-tetrazol-5-yl)methanol.

In a second aspect, the invention relates to a process for manufacturing a compound of formula (I) according to claim 1 comprising: starting from an epoxynitrile of formula (II):

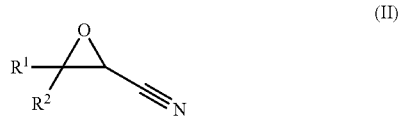

(II)

and performing the following steps:
  (a) reacting compound (II) with an azide in presence of an organometallic catalyst, and
  (b) performing an hydrolysis reaction to afford compound (I).

According to an embodiment, the azide is trimethylsilyl azide. According to an embodiment, the organometallic catalyst is dibutyltin oxide. According to an embodiment, step (a) is executed in a solvent, said solvent being toluene. According to an embodiment, step (a) is executed at 60° C. during 18 h. According to an embodiment, step (b) of hydrolysis is acidic hydrolysis.

In others aspects, the invention relates to an alpha-hydroxy-beta-triazole-tetrazole compound of formula (III):

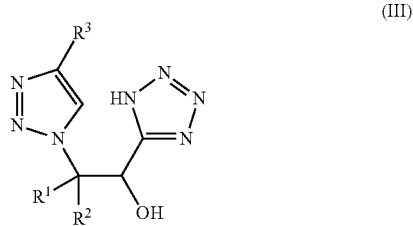

(III)

wherein R$^1$ and R$^2$ are each independently hydrogen, hydrocarbyl, aryl, heteroaryl, hydrocarbylaryl, arylhydrocarbyl, hydrocarbylheteroaryl, or heteroarylhydrocarbyl groups; or R$^1$ and R$^2$ form together a group being hydrocarbyl, aryl, heteroaryl, hydrocarbylaryl, arylhydrocarbyl, hydrocarbylheteroaryl, or heteroarylhydrocarbyl;
  wherein the groups are optionally substituted by at least one group being hydrocarbyl, aryl, heteroaryl, oxo, hydroxyl, amido, amino, nitro, carboxylo, formyl, halo, thioxo or sulfhydryl;
  wherein the groups are optionally interrupted or terminated by at least one group being —O—; —S—; and —NR$^N$— wherein R$^N$ is hydrogen, hydrocarbyl, aryl, or a combination thereof;
  wherein the nitrogen or sulfur atoms substituting or comprised in the group are optionally oxidized; and
wherein R$^3$ is hydrogen, an organic group or an organic molecule;
and stereoisomers thereof; and salts thereof; and solvates thereof.

According to an embodiment, R$^3$ is hydrogen, hydroxyl, amido, amino, cyano, tetrazolyl, triazolyl, nitro, borono, carboxylo, formyl, halo, haloformyl, phosphono, phosphate or sulfhydryl.

According to an embodiment, R$^3$ is hydrogen, hydrocarbyl, aryl, heteroaryl, hydrocarbylaryl, arylhydrocarbyl, hydrocarbylheteroaryl, or heteroarylhydrocarbyl; wherein the group is optionally substituted by at least one group being hydrocarbyl, heteroaryl, oxo, hydroxyl, amido, amino, cyano, tetrazolyl, triazolyl, nitro, carboxylo, formyl, halo, thioxo or sulfhydryl; and wherein the group is optionally interrupted or terminated by at least one group being —O—; —S—; and —NR$^N$— wherein R$^N$ is hydrogen, hydrocarbyl, aryl, or a combination thereof; and wherein the nitrogen or sulfur atoms substituting or comprised in the group are optionally oxidized.

According to an embodiment, R$^3$ is a carbohydrate, an amino acid, a peptide or a nucleoside.

According to an embodiment, R$^3$ is selected from the group consisting of alkyl, alkenyl, aryl, heteroaryl, alkylaryl, arylalkyl, alkenylaryl, arylalkenyl, alkylheteroaryl, and heteroarylalkyl groups; wherein the group is optionally substituted by at least one group selected from the group consisting of alkyl, alkenyl, aryl, heteroaryl, alkylaryl, arylalkyl, oxo, hydroxyl, amido, amino, tetrazolyl, triazolyl, nitro, carboxylo, formyl, halo, thioxo and sulfhydryl; and the group is optionally interrupted or terminated by at least one group selected from the group consisting of —O—; —S—; and —NR$^N$— wherein R$^N$ is selected from the group consisting of hydrogen, alkyl, alkenyl, aryl, and a combination thereof.

According to an embodiment, the alpha-hydroxy-beta-triazolo-tetrazole is selected from the group consisting of: (1-(4-phenyl-1H-1,2,3-triazol-1-yl)cyclohexyl)(1H-tetrazol-5-yl)methanol; (1-(4-phenyl-1H-1,2,3-triazol-1-yl)cycloheptyl)(1H-tetrazol-5-yl)methanol; (1-(4-phenyl-1H-1,2,3-triazol-1-yl)cyclooctyl)(1H-tetrazol-5-yl)methanol; tert-butyl 1-(1-(hydroxy(1H-tetrazol-5-yl)methyl)cyclooctyl)-1H-1,2,3-triazole-4-carboxylate; (1-(4-(3-chloropropyl)-1H-1,2,3-triazol-1-yl)cyclooctyl)(1H-tetrazol-5-yl)methanol; 2-(1-(1-(hydroxy(1H-tetrazol-5-yl)methyl)cyclooctyl)-1H-1,2,3-triazol-4-yl)ethan-1-ol; 2-ethyl-2-(4-phenyl-1H-1,2,3-triazol-1-yl)-1-(1H-tetrazol-5-yl)butan-1-ol; 2-(4-hexyl-1H-1,2,3-triazol-1-yl)-2-phenyl-1-(1H-tetrazol-5-yl)ethan-1-ol; 2-(4-hexyl-1H-1,2,3-triazol-1-yl)-2,2-diphenyl-1-(1H-tetrazol-5-yl)ethan-1-ol; 2-(4-(3-chloropropyl)-1H-1,2,3-triazol-1-yl)-2,2-diphenyl-1-(1H-tetrazol-5-yl)ethan-1-ol; or tert-butyl 1-(2-hydroxy-1,1-diphenyl-2-(1H-tetrazol-5-yl)ethyl)-1H-1,2,3-triazole-4-carboxylate.

In others aspects, the invention relates to a triazole alkyne of formula (IV):

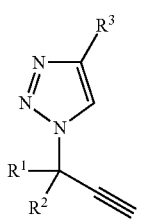

(IV)

wherein $R^1$ and $R^2$ are each independently groups as previously disclosed; or $R^1$ and $R^2$ form together a group as previously disclosed; and $R^3$ is a group as previously disclosed; and stereoisomers thereof; and salts thereof; and solvates thereof.

In others aspects, the invention relates to reactions, especially CuAAC reactions, wherein compounds (I), (III) and/or (IV) are used as reactants.

DEFINITIONS

In the present invention, the following terms have the following meanings:

"about" preceding a figure means plus or less 10% of the value of said figure.

"alkyl" refers to a linear, cyclic or branched saturated hydrocarbon chain of general formula—$C_nH_{2n+1}$ wherein n is a number greater than or equal to 1, typically containing 1 to 16 carbon atoms, preferably 1 to 12 carbon atoms, more preferably 1 to 8 carbon atoms. When concerning a group being bounded twice to the same carbon atom, "alkyl" also refers to an alkylenyl derived from an alkyl by removal of a hydrogen atom. Examples of alkyl groups are methyl, ethyl, n-propyl, isopropyl, butyl, pentyl, hexyl, cyclopentyl and 2-ethylcyclohexyl.

"alkenyl" refers to a linear, cyclic or branched unsaturated hydrocarbon chain, typically containing 1 to 16 carbon atoms, preferably 1 to 12 carbon atoms, more preferably 1 to 8 carbon atoms, wherein the unsaturation arises from the presence of one or more carbon-carbon double bonds. When concerning a group being bounded twice to the same carbon atom, "alkenyl" also refers to an alkenylenyl derived from an alkenyl by removal of a hydrogen atom. Examples of alkenyl groups are propenyl, butenyl, hexenyl and 3-ethylcyclohex-2-enyl.

"alkynyl" refers to a linear, cyclic or branched unsaturated hydrocarbon chain, typically containing 1 to 16 carbon atoms, preferably 1 to 12 carbon atoms, more preferably 1 to 8 carbon atoms, wherein the unsaturation arises from the presence of one or more carbon-carbon triple bonds. When concerning a group being bounded twice to the same carbon atom, "alkynyl" also refers to an alkynylenyl derived from an alkynyl by removal of a hydrogen atom. Examples of alkynyl groups are propynyl, butynyl, hexynyl and 3-ethylcyclohex-2-ynyl.

"amido" refers to —C(=O)—$NH_2$ group.

"amino" refers to —$NH_2$ group.

"aryl" refers to a polyunsaturated, aromatic hydrocarbon chain having a single ring (i.e. phenyl) or multiple rings fused together (e.g. naphtyl) or linked covalently, wherein at least one ring is aromatic, typically containing 5 to 16 carbon atoms, preferably 5 to 10 carbon atoms, more preferably 5 or 6 carbon atoms. "Aryl" also refers to the partially hydrogenated derivatives of the carbocyclic systems enumerated herein. Examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"azide" refers to a molecule comprising the azido group.

"azido" refers to —$N_3$ (—N=$N^{(+)}$=$N^{(-)}$) group.

"borono" refers to —$B(OH)_2$ group.

"carboxylo" refers to carboxylic acid —COOH group.

"cyano" or "carbonitrile" refers to group.

"cycloalkyl", "cycloalkenyl" and "cycloalkynyl" respectively refers to a cyclic or polycyclic alkyl, alkenyl and alkynyl group, typically containing 5 to 16 atoms, optionally branched. Examples of cycloalkyl are cyclopropyl, cyclopentyl and cyclohexyl.

"hydrocarbyl" refers to any alkyl, alkenyl or alkynyl group as defined above. Unless otherwise stated, any term defined in this section which include this term "hydrocarbyl" also define every corresponding term wherein "hydrocarbyl" is substituted by "alkyl", "alkenyl" or "alkynyl". For example, "halohydrocarbyl" as defined hereafter define simultaneously by similarity "haloalkyl", "haloalkenyl" and "haloalkynyl".

"heteroaryl" refers to an aryl group as defined above, wherein one or more carbon atoms in one or more aromatic rings are replaced by oxygen, nitrogen or sulfur atoms, and where the nitrogen and sulfur heteroatoms may optionally be oxidized and the nitrogen heteroatoms may optionally be quaternized. Non-limiting examples of such heteroaryl are pyrrolyl, furanyl, thiophenyl and pyrazolyl.

"hydrocarbylaryl" and "arylhydrocarbyl" respectively refers to an aryl group substituted by, or fused with, a hydrocarbyl group and to a hydrocarbyl group substituted by, or fused with, an aryl group.

"hydrocarbylheteroaryl" and "heteroarylhydrocarbyl" respectively refers to a heteroaryl group substituted by, or fused with, a hydrocarbyl group and to a hydrocarbyl group substituted by, or fused with, a heteroaryl group.

"aryloxyl" refers to —O-aryl group.

"hydrocarbyloxyl" refers to —O-hydrocarbyl group.

"haloaryl" refers to an aryl group as defined above, further comprising at least one halo group.

"halohydrocarbyl" refers to a hydrocarbyl group as defined above, further comprising at least one halo group.

"formyl" refers to aldehyde —CHO group.

"halo" refers to fluoride, chloride, bromide or iodide atoms.

"haloformyl" refers to —C(=O)X group, wherein X is halo group as defined above.

"hydroxyl" refers to —OH group.

"nitro" refers to —$NO_2$ group.

"nitrile" refers to a molecule comprising the cyano group.

"oxo" refers to =O group, i.e. an oxygen atom forming a double bond with a carbon atom.

"phosphono" refers to —P(=O)$(OH)_2$ group.

"phosphato" refers to —O—P(=O)$(OH)_2$ group.

"prodrug" refers to derivatives of a biologically active drug compound, such as for example amides, whose in vivo biotransformation product generates the biologically active drug. Prodrugs are generally characterized by increased bio-availability and are readily metabolized into biologically active compounds in vivo.

"protective group" refers to a functional group that masks the characteristic reactivity of another group to which it can later be converted. Examples of protecting groups are acetyl (Ac), benzoyl (Bz), tert-butyloxycarbonyl (BOC), carbobenzoyloxy (Cbz), p-methoxybenzyl ether (PMB), silyl ethers such as trimethylsilyl (TMS), tert-butyldimethylsilyl (TBDMS) and tetrahydropyranyl (THP).

"solvate" refers to a compound that contains stoichiometric or sub-stoichiometric amounts of one or more solvent molecule such as ethanol. The term "hydrate" refers to when the solvent is water.

"sulfhydryl" refers to —SH group.

"tetrazole" refers to a molecule comprising the tetrazolo group.

"tetrazolo" refers to a 5-member heterocyclic group, consisting of a ring of four nitrogen and one carbon atom of general formula CRR'N$_4$, wherein R and R' are either hydrogen or other groups.

"tetrazolyl" refers to the 5-member heterocyclic group —CHN$_4$.

"triazole" refers to a molecule comprising the triazolo group.

"triazolo" refers to a 5-member heterocyclic group, consisting of a ring of three nitrogen and two carbon atom, of general formula C$_2$RR'R"N$_3$., wherein R, R' and R" are either hydrogen or other groups.

"triazolyl" refers to the 5-member heterocyclic group —CH$_2$N$_3$.

"thioxo" refers to =S group, i.e. a sulfur atom forming a double bond with a carbon atom.

In the present invention, the following abbreviations have the following meanings:

"Ac" refers to acetyl group —C(=O)CH$_3$.

"Bu$_2$SnO" refers to dibutyltin oxide (C$_4$H$_9$)$_2$Sn=O [No. CAS: 818-08-6]

"CuAAC" refers to a copper-catalysed azide-alkyne cycloaddition reaction.

"EDC" refers to 1-ethyl-3-(3-dimethylaminopropyl)carbodiimide [No. CAS: 1892-57-5].

"Et" refers to ethyl —C$_2$H$_5$.

"EtOAc" refers to ethyl acetate [No. CAS: 141-78-6].

"DCC" refers to N,N'-dicyclohexylcarbodiimide [No. CAS: 538-75-0].

"DIC" refers to N, N'-diisopropylcarbodiimide [No. CAS: 693-13-0].

"NaAs" refers to sodium ascorbate [No. CAS: 134-03-2 (L)].

"Ph" refers to phenyl —C$_6$H$_5$.

"TBTA" refers to tris(benzyltriazolylmethyl)amine [No. CAS: 510758-28-8].

"TMSN$_3$" refers to trimethylsilyl azide (CH$_3$)$_3$SiN$_3$ [No. CAS: 4648-54-8].

DETAILED DESCRIPTION

Alpha-Hydroxy-Beta-Azido Tetrazoles

In its first aspect, the invention relates to alpha-hydroxy-beta-azido tetrazoles of formula (I):

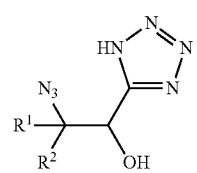

wherein $R^1$ and $R^2$ are each independently hydrogen, hydrocarbyl, aryl, heteroaryl, hydrocarbylaryl, arylhydrocarbyl, hydrocarbylheteroaryl, or heteroarylhydrocarbyl groups; or $R^1$ and $R^2$ form together a group being hydrocarbyl, aryl, heteroaryl, hydrocarbylaryl, arylhydrocarbyl, hydrocarbylheteroaryl, or heteroarylhydrocarbyl; and the group is optionally substituted by at least one group being hydrocarbyl, aryl, heteroaryl, oxo, hydroxyl, amido, amino, azido, cyano, nitro, borono, carboxylo, formyl, halo, haloformyl, phosphono, phosphato, thioxo or sulfhydryl; and the group is optionally interrupted or terminated by at least one group being —B(OR$^B$)— with R$^B$ being hydrogen, hydrocarbyl, aryl or a combination thereof; —O—; —PR$^P$— with R$^P$ being hydrogen, hydrocarbyl, aryl or a combination thereof; —P(OR$^{OP}$)— with R$^{OP}$ being hydrogen, hydrocarbyl, aryl or a combination thereof; —S—; —NR$^N$— with R$^N$ being hydrogen, hydrocarbyl, aryl, or a combination thereof; or a combination thereof; and the nitrogen, phosphorus or sulfur atoms substituting or comprised in the group are optionally oxidized.

The invention also relates to any stereoisomers, salts, solvates, and prodrugs of a compound of formula (I), including quaternary ammonium salts.

The compounds of the invention may contain one or more asymmetric center and may thus exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of salts. Salts of the compounds of the invention include the acid addition and base salts thereof. Suitable acid addition salts are formed from acids. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen, phosphate/dihydrogen, phosphate, pyroglutamate, saccharate, stearate, succinate, tannate, tartrate, tosylate, trifluoroacetate and xinofoate salts. Suitable base salts are formed from bases. Examples include the aluminium, arginine, benzathine, calcium, choline, diethylamine, diolamine, glycine, lysine, magnesium, meglumine, olamine, potassium, sodium, trometamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule. Preferred salts include hydrochloride/chloride, hydrobromide/bromide, bisulphate/sulphate, nitrate, citrate, and acetate.

Salts of compounds of the invention may be prepared by one or more of these methods:
(i) by reacting the compound of the invention with the desired acid;
(ii) by reacting the compound of the invention with the desired base;
(iii) by removing an acid- or base-labile protecting group from a suitable precursor of the compound of the invention or by ring-opening a suitable cyclic precursor, for example, a lactone or lactam, using the desired acid; or
(iv) by converting one salt of the compound of the invention to another by reaction with an appropriate acid or by means of a suitable ion exchange column.

Optionally, one or more alkene, alkyne, oxo, hydroxyl, amido, amino, azido, nitro, borono, carboxylo, formyl, halo, haloformyl, phosphono, phosphato, thioxo or sulfhydryl being present in compound (I) is protected by any suitable protecting group known by a skilled person of the art.

According to an embodiment, $R^1$ and $R^2$ are each independently hydrogen, hydrocarbyl, aryl, heteroaryl, hydrocarbylaryl, arylhydrocarbyl, hydrocarbylheteroaryl, or heteroarylhydrocarbyl groups; and
the groups are optionally substituted by at least one group being hydrocarbyl, aryl, heteroaryl, oxo, hydroxyl, amido, amino, nitro, carboxylo, formyl, halo, thioxo or sulfhydryl; and
the groups are optionally interrupted or terminated by at least one group being —O—; —S—; and —NR$^N$— with R$^N$ being hydrogen, hydrocarbyl, aryl, or a combination thereof; and
the nitrogen or sulfur atoms substituting or comprised in the groups are optionally oxidized.

According to a specific embodiment, $R^1$ and $R^2$ are each independently selected from the group consisting of hydrogen, alkyl, alkenyl, aryl, heteroaryl, alkylaryl, arylalkyl, alkenylaryl, and arylalkenyl groups;
the groups are optionally substituted by at least one group selected from the group consisting of hydroxyl, alkyl, alkenyl, aryl, alkylaryl, arylalkyl, amino, nitro, halo and sulfhydryl; and
the groups are optionally interrupted or terminated by at least one group selected from the group consisting of —O—; —S—; and —NR$^N$— with R$^N$ being selected from the group consisting of hydrogen, alkyl, alkenyl, aryl, and a combination thereof.

According to a more specific embodiment, $R^1$ and $R^2$ are each independently selected from the group consisting of hydrogen, alkyl, alkenyl, aryl, heteroaryl, alkylaryl and alkenylaryl groups; and the groups are optionally substituted by at least one group selected from the group consisting of hydroxyl, alkyl, amino, nitro, halo and sulfhydryl; and the groups are optionally interrupted or terminated by at least one group selected from the group consisting of —O—; —S—; and —NR$^N$— with R$^N$ being selected from the group consisting of hydrogen, alkyl, alkenyl, aryl, alkylaryl, and arylalkyl.

According to a furthermore specific embodiment, $R^1$ and $R^2$ are each independently selected from the group consisting of hydrogen, alkyl, aryl and alkenylaryl groups; and the groups are optionally substituted by at least one halo group.

According to a furthermore specific embodiment, the alpha-hydroxy-beta-azido tetrazole is selected from the group consisting of:
2-azido-2-phenyl-1-(1H-tetrazol-5-yl)ethan-1-ol;
2-azido-2-(naphthalen-2-yl)-1-(1H-tetrazol-5-yl)ethan-1-ol;
2-azido-2-(4-chlorophenyl)-1-(1H-tetrazol-5-yl)ethan-1-ol;
2-azido-1-(1H-tetrazol-5-yl)-2-(thiophen-2-yl)ethan-1-ol;
2-azido-4-phenyl-1-(1H-tetrazol-5-yl)but-3-en-1-ol;
2-azido-1-(1H-tetrazol-5-yl)nonan-1-ol;
2-azido-2-ethyl-1-(1H-tetrazol-5-yl)butan-1-ol; and
2-azido-2,2-diphenyl-1-(1H-tetrazol-5-yl)ethan-1-ol.

According to an embodiment, $R^1$ and $R^2$ form together a group being hydrocarbyl, aryl, heteroaryl, hydrocarbylaryl, arylhydrocarbyl, hydrocarbylheteroaryl, or heteroarylhydrocarbyl; and
the group is optionally substituted by at least one group being hydrocarbyl, aryl, heteroaryl, oxo, hydroxyl, amido, amino, nitro, carboxylo, formyl, halo, thioxo or sulfhydryl; and
the group is optionally interrupted or terminated by at least one group being —O—; —S—; and —NR$^N$— with R$^N$ being hydrogen, hydrocarbyl, aryl, or a combination thereof; and
the nitrogen or sulfur atoms substituting or comprised in the group are optionally oxidized.

According to a specific embodiment, $R^1$ and $R^2$ form together a group selected from the group consisting of alkyl, alkenyl, aryl, alkylaryl, arylalkyl, alkenylaryl and arylalkenyl;
the group is optionally substituted by at least one group selected from the group consisting of hydroxyl, alkyl, alkenyl, aryl, alkylaryl, arylalkyl, amino, nitro, halo and sulfhydryl; and
the group is optionally interrupted or terminated by at least one group selected from the group consisting of —O—; —S—; and —NR$^N$— with R$^N$ being selected from the group consisting of hydrogen, alkyl, alkenyl, aryl, and a combination thereof.

According to a more specific embodiment, $R^1$ and $R^2$ form together a group selected from the group consisting of alkyl, alkylaryl and arylalkyl; and the group is optionally substituted by at least one group selected from the group consisting of hydroxyl, alkyl, amino, nitro and halo; and the group is optionally interrupted or terminated by at least one group selected from the group consisting of —O— and —NR$^N$— with R$^N$ being selected from the group consisting of hydrogen, alkyl, alkenyl, aryl, alkylaryl, and arylalkyl.

According to a furthermore specific embodiment, $R^1$ and $R^2$ form together a group selected from the group consisting of alkyl and aryl.

According to a furthermore specific embodiment, alpha-hydroxy-beta-azido tetrazole is:
(1-azidocyclopentyl)(1H-tetrazol-5-yl)methanol;
(1-azidocyclohexyl)(1H-tetrazol-5-yl)methanol;
(1-azidocycloheptyl)(1H-tetrazol-5-yl)methanol;
(1-azidocyclooctyl)(1H-tetrazol-5-yl)methanol; or
(9-azido-9H-fluoren-9-yl)(1H-tetrazol-5-yl)methanol.

According to an embodiment, one or more amino, hydroxyl, or sulfhydryl group being present in compound (I) is protected by any suitable protecting group known by a skilled person of the art.

According to a specific embodiment, one or more amino group being present in compound (I) is protected by a protective group selected from: benzyl (CH$_2$Ph), p-methoxybenzyl ether (PMB), tert-butyloxycarbonyl (BOC), carbobenzoyloxy (Cbz) and tosyl (Ts).

According to a specific embodiment, one or more hydroxyl group being present in compound (I) is protected by a protective group being benzyl (CH$_2$Ph), p-methoxybenzyl ether (PMB), tetrahydropyranyl (THP) and silyl ethers such as trimethylsilyl (TMS, SiMe$_3$), tert-butyldimethylsilyl (TBDMS, SitBu(Me)$_2$), triethylsilyl (TES, SiEt$_3$), methyldiphenylsilyl (SiPh$_2$Me) or tri-isopropylsilyl (TIPS, Si(iPr)$_3$).

According to a specific embodiment, one or more sulfhydryl group being present in compound (I) is protected by a protective group being benzyl (CH$_2$Ph), p-methoxybenzyl ether (PMB), triphenylmethyl ((C$_6$H$_5$)$_3$C) or tetrahydropyranyl (THP).

The alpha-hydroxy-beta-azido tetrazoles according to the invention may be prepared by the process of manufacturing according to the invention, as disclosed hereafter.

The alpha-hydroxy-beta-azido tetrazoles according to the invention may be used as reactants, as disclosed hereafter.

Synthesis of Alpha-Hydroxy-Beta-Azido Tetrazoles

The most popular way to efficiently produce tetrazoles is the cycloaddition of azides with nitriles. Various improvements have appeared, including the use of sodium azide or trimethylsilyl azide (TMSN$_3$) with ammonium chloride, zinc dibromide, trimethyl aluminium, or silver nitrate. However, these reactions are promoted either by Brønsted or Lewis acids and may thus be unsuitable for cycloaddition of sensible nitriles. Some of the azide sources may also cause safety issues. Microwave irradiation has also been used, but this reaction requires elevated temperatures (above 100° C.).

Another possibility lies in the use of dibutyltin oxide (Bu$_2$SnO) as a catalyst, in conjunction with trimethylsilyl azide (TMSN$_3$), as described by Wittenberger et al. (Wittenberger, S. J. et al., Journal of Organic Chemistry, 1993, Vol. 58, pp. 4139-4141.). In contrast to the above methods, this reaction involves neutral reaction medium and a weak Lewis acid, thus allowing cycloaddition of nitriles fitted with a Lewis base. This reaction has been applied to the synthesis of aryl tetrazoles and of unsubstituted aliphatic tetrazoles, but had never been applied to the synthesis of alpha-hydroxy-beta-azido-tetrazoles.

In its second aspect, the invention relates to a process for manufacturing an alpha-hydroxy-beta-azido-tetrazole as disclosed in previous section entitled "Alpha-hydroxy-beta-azido-tetrazoles", comprising carrying out the reaction between an alpha, beta-epoxynitrile and an azide in presence of a catalyst.

According to an embodiment, the invention relates to a process for manufacturing an alpha-hydroxy-beta-azido tetrazole of formula (I):

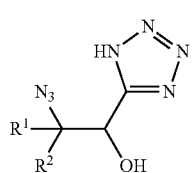

(I)

comprising starting from an epoxynitrile of formula (II):

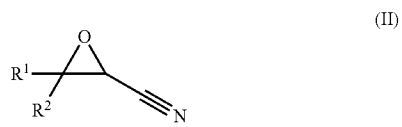

(II)

wherein R$^1$ and R$^2$ are each independently groups as disclosed in previous section; or R$^1$ and R$^2$ form together a group as disclosed in previous section;

and performing the following steps:
(a) reacting compound (II) with an azide in presence of an organometallic catalyst,
(b) performing a hydrolysis reaction to afford compound (I).

This process is schematically represented below:

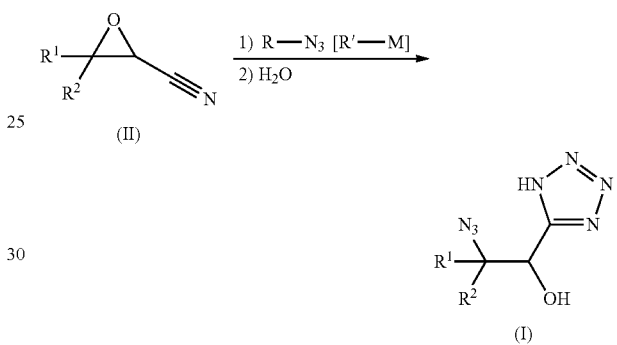

Epoxynitriles compounds (II) can be synthesized by any suitable process known by the skilled person of the art, e.g. by Darzens reaction as proposed by Alcaide et al. (Alcaide et al., Tetrahedron Lett., 1995, 36, 5417).

According to an embodiment, the azide is organic, inorganic or organometallic. According to a specific embodiment, the azide is sodium azide or trimethylsilyl azide (TMSN$_3$). According to a more specific embodiment, the azide is trimethylsilyl azide.

According to an embodiment, the azide/epoxynitrile molar ratio in the reaction medium ranges from 20 to 1. According to a specific embodiment, the azide/epoxynitrile ratio ranges from 6 to 4. According to a more specific embodiment, the azide/epoxynitrile ratio is about 3 (i.e. about 3 equiv. of azide for 1 equiv. of epoxynitrile).

According to an embodiment, the catalyst is a metal oxide. According to a specific embodiment, the catalyst an dialkyltin oxide of general formula (alkyl)$_2$SnO, such as dibutyltin oxide (Bu$_2$SnO) and dimethyltin oxide (Me$_2$SnO). According to a more specific embodiment, the catalyst is dibutyltin oxide.

According to an embodiment, the catalyst/epoxynitrile molar ratio in the reaction medium ranges from 5 to 0.01. According to another specific embodiment, the catalyst/epoxynitrile ratio ranges from 2 to 0.1. According to a more specific embodiment, the catalyst/epoxynitrile ratio is about 0.5 (i.e. about 0.5 equiv. of catalyst for 1 equiv. of epoxynitrile).

According to an embodiment, the step of reacting an epoxynitrile with an azide is executed in a solvent. According to a specific embodiment, the solvent is tetrahydrofurane (THF), chloroform, 1,2-dichloroethane, 1,4-dioxane, toluene or mixtures thereof. According to a more specific embodiment, the solvent is toluene.

According to an embodiment, the step of reacting an epoxynitrile with an azide is executed in a duration ranging from 4 h to 72 h. According to a specific embodiment, the duration ranges from 12 h to 24 h. According a more specific embodiment, the duration is about 18 h.

According to an embodiment, the step of reacting an epoxynitrile with an azide is executed at a temperature ranging from 25 to 100° C. According to a specific embodiment, the temperature ranges from 40 to 80° C. According to a more specific embodiment, the temperature is about 60° C.

According to a specific embodiment, the hydrolysis reaction is an acidic hydrolysis reaction. According to a specific embodiment, the reaction is performed by using an acid being sulphuric acid, acetic acid, trifluoroacetic acid or hydrochloric acid (HCl); or aqueous solutions thereof; or organic solutions thereof. According to a more specific embodiment, the hydrolysis is achieved through treatment by an aqueous hydrochloric acid solution, such as a 2N HCl solution.

According to a specific embodiment, the invention relates to a process for manufacturing an alpha-hydroxy-beta-azido tetrazole of formula (I) as previously disclosed, comprising starting from an epoxynitrile of formula (II) as previously disclosed and performing the following steps:
(a) reacting compound (II) with TMSN$_3$ in toluene in presence of Bu$_2$SnO,
(b) performing an acidic hydrolysis reaction to afford compound (I).

According to an embodiment, the reaction between the epoxynitrile and the azide is regioselective. According to an embodiment, the reaction between the epoxynitrile and the azide is stereoselective.

According to a specific embodiment, the reaction between the epoxynitrile and the azide is both regioselective and stereoselective.

Use of Alpha-Hydroxy-Beta-Azido-Tetrazoles in "Click" Reactions

The invention also relates to the use of alpha-hydroxy-beta-azido-tetrazoles as reactants for synthesis, especially in "click" reactions such as CuAAC.

Alpha-Hydroxy-Beta-Triazolo-Tetrazoles —CuAAC Reaction

In its third aspect, the invention relates to an alpha-hydroxy-beta-triazolo-tetrazole of formula (III):

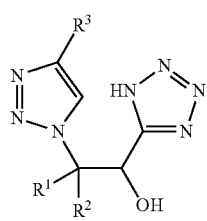

(III)

wherein R$^1$ and R$^2$ are each independently groups as disclosed in previous section; or R$^1$ and R$^2$ form together a group as disclosed in previous section; and
wherein R$^3$ is hydrogen; an organic group such as alkyl, hydroxyl or amino; an organic molecule such as a polymer, a carbohydrate, a protein, an amino acid, a peptide, a nucleoside; an inorganic compound such as a metal salt; or an organometallic compound such as a metal complex.

The invention also relates to any stereoisomers, salts, solvates, and prodrugs of a compound of formula (III), including quaternary ammonium salts.

According to an embodiment, R$^3$ is hydrogen, an organic group or an organic molecule.

According to an embodiment, R$^3$ is hydrogen, hydroxyl, amido, amino, cyano, tetrazolyl, triazolyl, nitro, carboxylo, formyl, halo or sulfhydryl.

According to an embodiment, R$^3$ is any independent R$^1$ or R$^2$ group as previously disclosed.

According to an embodiment, R$^3$ is hydrogen, hydrocarbyl, aryl, heteroaryl, hydrocarbylaryl, arylhydrocarbyl, hydrocarbylheteroaryl, or heteroarylhydrocarbyl group;
the group is optionally substituted by at least one group being hydrocarbyl, aryl, heteroaryl, oxo, hydroxyl, amido, amino, azido, cyano, tetrazolyl, triazolyl, nitro, borono, carboxylo, formyl, halo, haloformyl, phosphono, phosphato, thioxo or sulfhydryl;
the group is optionally interrupted or terminated by at least one group being —B(OR$^B$)— with R$^B$ being hydrogen, hydrocarbyl, aryl or a combination thereof; —O—; —PR$^P$— with R$^P$ being hydrogen, hydrocarbyl, aryl or a combination thereof; —P(OR$^{OP}$)— with R$^{OP}$ being hydrogen, hydrocarbyl, aryl or a combination thereof; —S—; —NR$^N$— with R$^N$ being hydrogen, hydrocarbyl, aryl or a combination thereof; or a combination thereof; and
the nitrogen, phosphorus or sulfur atoms substituting or comprised in the group are optionally oxidized.

According to an embodiment, R$^3$ is hydrogen, hydrocarbyl, aryl, heteroaryl, hydrocarbylaryl, arylhydrocarbyl, hydrocarbylheteroaryl, or heteroarylhydrocarbyl group;
the group is optionally substituted by at least one group being hydrocarbyl, aryl, heteroaryl, oxo, hydroxyl, amido, amino, tetrazolyl, triazolyl, nitro, carboxylo, formyl, halo, thioxo or sulfhydryl; and
the group is optionally interrupted or terminated by at least one group being —O—; —S—; and —NR$^N$— with R$^N$ being hydrogen, hydrocarbyl, aryl, or a combination thereof; and the nitrogen or sulfur atoms substituting or comprised in the group are optionally oxidized.

According to a specific embodiment, R$^3$ is selected from the group consisting of alkyl, alkenyl, aryl, heteroaryl, alkylaryl, arylalkyl, alkenylaryl, arylalkenyl, alkylheteroaryl, and heteroarylalkyl groups; and
the group is optionally substituted by at least one group selected from the group consisting of alkyl, alkenyl, aryl, heteroaryl, alkylaryl, arylalkyl, oxo, hydroxyl, amido, amino, tetrazolyl, triazolyl, nitro, carboxylo, formyl, halo, thioxo and sulfhydryl; and
the group is optionally interrupted or terminated by at least one group selected from the group consisting of —O—; —S—; and —NR$^N$— with R$^N$ being selected from the group consisting of hydrogen, alkyl, alkenyl, aryl, and a combination thereof.

According to a more specific embodiment, R$^3$ is selected from the group consisting of alkyl, aryl, and alkylaryl groups; and the groups are optionally substituted by at least one group selected from the group consisting of oxo, hydroxyl, alkyl, amino and halo; and the groups are optionally interrupted or terminated by at least one group selected from the group consisting of —O— and —NR$^N$— with R$^N$ being selected from the group consisting of hydrogen, alkyl, alkenyl, aryl, alkylaryl, and arylalkyl.

According to a furthermore specific embodiment, R$^3$ is selected from the group consisting of alkyl and aryl; and the groups are optionally substituted by at least one group selected from the group consisting of oxo, hydroxyl, alkyloxyl, and halo.

According to a furthermore specific embodiment, compound (III) is selected from the group consisting of:
(1-(4-phenyl-1H-1,2,3-triazol-1-yl)cyclohexyl)(1H-tetrazol-5-yl)methanol;
(1-(4-phenyl-1H-1,2,3-triazol-1-yl)cycloheptyl)(1H-tetrazol-5-yl)methanol;
(1-(4-phenyl-1H-1,2,3-triazol-1-yl)cyclooctyl)(1H-tetrazol-5-yl)methanol;
tert-butyl 1-(1-(hydroxy(1H-tetrazol-5-yl)methyl)cyclooctyl)-1H-1,2,3-triazole-4-carboxylate;
(1-(4-(3-chloropropyl)-1H-1,2,3-triazol-1-yl)cyclooctyl)(1H-tetrazol-5-yl)methanol;
2-(1-(1-(hydroxy(1H-tetrazol-5-yl)methyl)cyclooctyl)-1H-1,2,3-triazol-4-yl)ethan-1-ol;
2-ethyl-2-(4-phenyl-1H-1,2,3-triazol-1-yl)-1-(1H-tetrazol-5-yl)butan-1-ol;
2-(4-hexyl-1H-1,2,3-triazol-1-yl)-2-phenyl-1-(1H-tetrazol-5-yl)ethan-1-ol;
2-(4-hexyl-1H-1,2,3-triazol-1-yl)-2,2-diphenyl-1-(1H-tetrazol-5-yl)ethan-1-ol;
2-(4-(3-chloropropyl)-1H-1,2,3-triazol-1-yl)-2,2-diphenyl-1-(1H-tetrazol-5-yl)ethan-1-ol; and
tert-butyl 1-(2-hydroxy-1,1-diphenyl-2-(1H-tetrazol-5-yl)ethyl)-1H-1,2,3-triazole-4-carboxylate.

According to an embodiment, $R^3$ is a carbohydrate, an amino acid, a peptide or a nucleoside.

According to an embodiment, one or more amino, hydroxyl or sulfhydryl group being present in compound (III) is protected by any suitable protecting group known by a skilled person of the art. According to a specific embodiment, one or more amino group being present in compound (III) is protected by a protective group being benzyl ($CH_2Ph$), p-methoxybenzyl ether (PMB), tert-butyloxycarbonyl (BOC), carbobenzoyloxy (Cbz) or tosyl (Ts). According to another specific embodiment, one or more hydroxyl group being present in compound (III) is protected by a protective group being benzyl ($CH_2Ph$), p-methoxybenzyl ether (PMB), tetrahydropyranyl (THP) or silyl ether such as trimethylsilyl (TMS, $SiMe_3$), tert-butyldimethylsilyl (TBDMS, $SitBu(Me)_2$), triethylsilyl (TES, $SiEt_3$), methyldiphenylsilyl ($SiPh_2Me$) or tri-isopropylsilyl (TIPS, $Si(iPr)_3$). According to another specific embodiment, one or more sulfhydryl group being present in compound (III) is protected by a protective group being benzyl ($CH_2Ph$), p-methoxybenzyl ether (PMB), triphenylmethyl (($C_6H_5)_3C$) or tetrahydropyranyl (THP).

In its fourth aspect, the invention relates to a process for manufacturing a alpha-hydroxy-beta-triazolo-tetrazole, comprising carrying out the reaction between an alpha-hydroxy-beta-azido-tetrazole and a terminal alkyne in presence of a copper(I) source and a tertiary amine.

According to an embodiment, the invention relates to a process for manufacturing an alpha-hydroxy-beta-triazolo-tetrazole of formula (III):

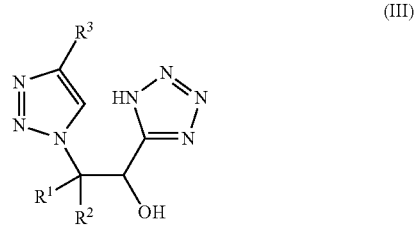

comprising starting from an alpha-hydroxy-beta-azido-tetrazole of formula (I):

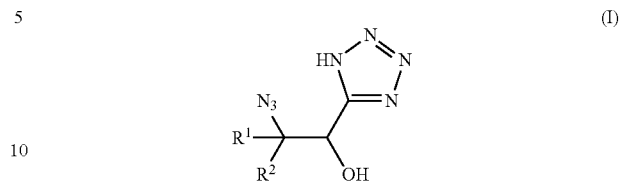

wherein $R^1$ and $R^2$ are each independently groups as previously disclosed; or $R^1$ and $R^2$ form together a group as previously disclosed;
and a terminal alkyne of formula $R^3$—C≡C—H,
wherein $R^3$ is as previously disclosed; and
carrying out the reaction of compound (I) with alkyne $R^3$—C≡C—H in presence of a copper(I) source and a tertiary amine, wherein the copper(I) source is either:
a combination of a copper(I) salt and a base, or
a combination of a copper(II) salt and a reducing agent.

This process is schematically represented below (L referring to the tertiary amine):

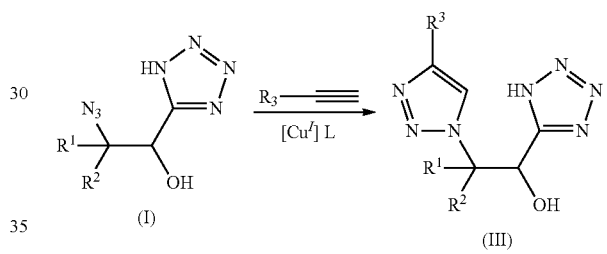

According to an embodiment, the copper(I) salt is copper (I) chloride, copper(I) bromide (CuBr) or copper(I) acetate; and the base is a basic amine such as N,N-diisopropylethylamine (DIEA). According to a specific embodiment, the copper salt is copper(I) bromide and the base is N,N-diisopropylethylamine According to another embodiment, the copper(II) salt is copper(II) chloride, copper(II) bromide, copper(II) acetate or copper(II) sulphate ($Cu^{II}SO_4$); and the reducing agent is sodium ascorbate (NaAs) or tri(2-carboxyethyl)phosphine (TECP). According to a specific embodiment, the copper salt is copper(II) sulphate and the reducing agent is sodium ascorbate.

According to an embodiment, the tertiary amine is tris (benzyltriazolylmethyl)amine (TBTA), tris(tertbutyltriazolylmethyl)amine (TTTA), tris(benzimidazole)methyl amine (TBIA), 4,7-diphenyl-1,10-phenanthroline-disulfonic acid disodium salt, tris [2-(N,N-dibenzylamino)ethyl]amine or tris(benzyltriazolylmethyl)amine According to a specific embodiment, the tertiary amine is tris(benzyltriazolylmethyl)amine (TBTA).

According to an embodiment, the alkyne/azide molar ratio in the reaction medium ranges from 1 to 10. According to a specific embodiment, the alkyne/azide ratio ranges from 2 to 5. According to a more specific embodiment, the alkyne/azide ratio is about 3 (i.e. about 3 equiv. of alkyne for 1 equiv. of azide).

According to an embodiment, the copper salt/azide molar ratio in the reaction medium ranges from 0.01 to 2. According to a specific embodiment, the copper salt/azide ratio ranges from 0.05 to 0.2. According to a more specific embodiment, the copper salt/azide ratio is about 0.1 (i.e. about 0.1 equiv. of copper salt for 1 equiv. of azide).

According to an embodiment, the copper salt/tertiary amine molar ratio in the reaction medium ranges from 0.1 to 10. According to a specific embodiment, the copper salt/tertiary amine ratio ranges from 0.5 to 2. According to a more specific embodiment, the copper salt/tertiary amine ratio is about 1 (i.e. about 1 equiv. of copper salt for 1 equiv. of tertiary amine)

According to an embodiment, the copper salt/reducing agent molar ratio in the reaction medium ranges from 0.1 to 2. According to a specific embodiment, the copper salt/reducing agent ratio ranges from 0.25 to 0.75. According to a more specific embodiment, the copper salt/reducing agent ratio is about 0.5 (i.e. about 0.5 equiv. of copper salt for 1 equiv. of reducing agent).

According to an embodiment, the step of carrying out the reaction between the alpha-hydroxy-beta-azido-tetrazole and the terminal alkyne is executed in a solvent. According to a specific embodiment, the solvent is ethanol, tetrahydrofuran (THF), N,N'-dimethylformamide (DMF), acetonitrile, n-butyl alcohol (n-BuOH), water or mixtures thereof. According to a more specific embodiment, the solvent is a mixture of n-butyl alcohol and water.

According to an embodiment, the step of carrying out the reaction between the alpha-hydroxy-beta-azido-tetrazole and the terminal alkyne is executed in a duration ranging from 12 h to 5 days. According to a specific embodiment, the duration ranges from 24 h to 72 h. According a more specific embodiment, the duration is about 48 h.

According to an embodiment, the step of carrying out the reaction between the alpha-hydroxy-beta-azido-tetrazole and the terminal alkyne is executed at a temperature ranging from 0 to 50° C. According to a specific embodiment, the temperature ranges from 15 to 30° C. According to a more specific embodiment, the temperature is room temperature, i.e. about 25° C.

According to an embodiment, the step of carrying out the reaction between the alpha-hydroxy-beta-azido-tetrazole and the terminal alkyne is executed under a suitable inert gas, such as argon.

According to a specific embodiment, the invention relates to a process for manufacturing a alpha-hydroxy-beta-triazolo-tetrazole of formula (III) as previously disclosed comprising starting from an alpha-hydroxy-beta-azido-tetrazole of formula (I) and a terminal alkyne of formula $R^3$—C≡C—H as previously disclosed, and carrying out the reaction of compound (II) with alkyne $R^3$—C≡C—H in presence of $Cu^{II}SO_4$, TBTA and NaAs in a n-BuOH/$H_2O$ mixture.

During the reaction described in this aspect of the invention, the hydroxy-tetrazole group acts as a "latent" or "hidden" alkyne group, meaning that it may be easily converted to an alkyne (as described hereafter) but does not react under CuAAC conditions.

Triazole Alkynes—Hydroxy-Tetrazole to Alkyne Reaction

Wardrop et al. described the conversion of alpha-hydroxy-tetrazoles to alkynes through a [1,2]-rearrangement process using carbodiimides, which are compounds of general formula RN═C═NR, as dehydrating agents (Wardrop, D. J. et al., Organic Letters, 2012, Vol. 14, No. 6, pp. 1548-1551.). From alpha-hydroxy-alpha-aryl tetrazoles, this reaction allowed the preparation of internal alkynes substituted by at least one aryl group, most conveniently using diisopropyl-carbodiimide (DIC). However, instead of forming this alkyne, this process could also lead to a 5-membered cycle or heterocycle, by a cyclisation mechanism involving an [1,5]-C—H insertion.

In its fifth aspect, the invention relates to a triazole alkyne of formula (IV):

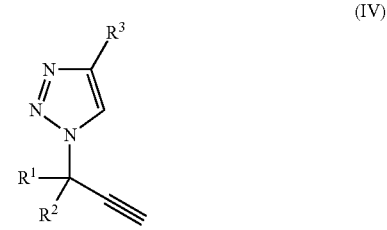

(IV)

wherein $R^1$ and $R^2$ are each independent groups as disclosed in previous section; or $R^1$ and $R^2$ form together a group as disclosed in previous section; and $R^3$ is as disclosed in previous section.

The invention also relates to any stereoisomers, salts, solvates, and prodrugs of a compound of formula (IV), including quaternary ammonium salts.

According to a furthermore specific embodiment, the triazole alkynes manufactured by the process are selected from the group consisting of:

1-(1-ethynylcyclohexyl)-4-phenyl-1H-1,2,3-triazole;

1-(1-ethynylcycloheptyl)-4-phenyl-1H-1,2,3-triazole;

1-(1-ethynylcyclooctyl)-4-phenyl-1H-1,2,3-triazole;

tert-butyl 1-(1-ethynylcyclooctyl)-1H-1,2,3-triazole-4-carboxylate;

4-(3-chloropropyl)-1-(1-ethynylcyclooctyl)-1H-1,2,3-triazole;

2-(1-(1-ethynylcyclooctyl)-1H-1,2,3-triazol-4-yl)ethan-1-ol;

1-(3-ethylpent-1-yn-3-yl)-4-phenyl-1H-1,2,3-triazole;

4-hexyl-1-(1-phenylprop-2-yn-1-yl)-1H-1,2,3-triazole; and 1-(1,1-diphenylprop-2-yn-1-yl)-4-hexyl-1H-1,2,3-triazole.

In its sixth aspect, the invention relates to a process for manufacturing a triazole alkyne, comprising carrying out the reaction between an alpha-hydroxy-beta-triazolo-tetrazole and a carbodiimide.

According to an embodiment, the invention relates to a process for manufacturing a triazole alkyne of formula (IV):

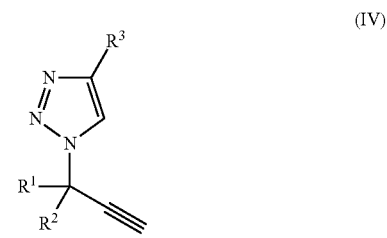

(IV)

comprising starting from an alpha-hydroxy-beta-triazolo-tetrazole of formula (III):

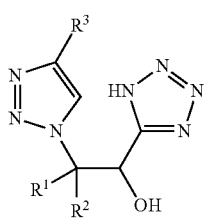

(III)

wherein R¹ and R² are each independent groups as previously disclosed; or R¹ and R² form together a group as previously disclosed; and R₃ is as previously disclosed; and carrying out the reaction of compound (III) with a carbodiimide.

This process is schematically represented below:

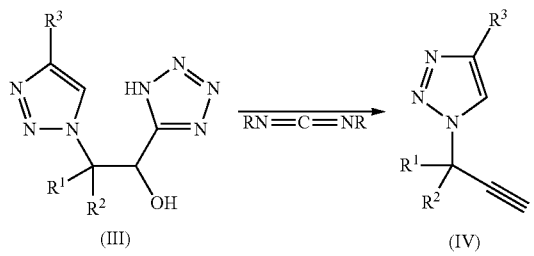

According to an embodiment, the carbodiimide is N,N'-dicyclohexylcarbodiimide (DCC), N, N'-diisopropylcarbodiimide (DIC), 1-ethyl-3-(3-dimethylaminopropyl)carbodiimide (EDC), phenyl ethyl carbodiimide (PEC), phenyl isopropyl carbodiimide (PIC), tert-butyl ethyl carbodiimide (BEC) or tert-butyl methyl carbodiimide (BMC). According to a specific embodiment, the carbodiimide is EDC.

According to an embodiment, the carbodiimide/tetrazole molar ratio in the reaction medium ranges from 0.5 to 5. According to a specific embodiment, the carbodiimide/tetrazole ratio ranges from 1 to 1.5. According to a more specific embodiment, the carbodiimide/tetrazole ratio is about 1.2 (i.e. about 1.2 equiv. of carbodiimide for 1 equiv. of tetrazole).

According to an embodiment, the step of carrying out the reaction between the alpha-hydroxy-beta-triazolo-tetrazole and the carbodiimide is executed in a solvent. According to a specific embodiment, the solvent is: chloroform, 1,2-dichloroethane, dichloromethane or mixture thereof. According to a more specific embodiment, the solvent is dichloromethane According to an embodiment, the step of carrying out the reaction between the alpha-hydroxy-beta-triazolo-tetrazole and the carbodiimide is executed in a duration ranging from 4 h to 72 h. According to a specific embodiment, the duration ranges from 12 h to 24 h. According a more specific embodiment, the duration is about 18 h.

According to an embodiment, the step of carrying out the reaction between the alpha-hydroxy-beta-triazolo-tetrazole and the carbodiimide is executed at a temperature ranging from 0 to 50° C. According to a specific embodiment, the temperature ranges from 15 to 30° C. According to a more specific embodiment, the temperature is room temperature, i.e. about 25° C.

According to a specific embodiment, the invention relates to a process for manufacturing an triazole alkyne of formula (IV) as previously disclosed, comprising starting from an alpha-hydroxy-beta-triazolo-tetrazole of formula (III) as previously disclosed, and carrying out the reaction of compound (III) with EDC in dichloromethane.

The reaction described in this aspect of the invention allows the conversion of the hydroxy-tetrazole to an alkyne, revealing the "latent" or "hidden" alkyne group of the alpha-hydroxy-beta-azido-tetrazole.

Multi-Triazoles —Further CuAAC Reactions

In its seventh aspect, the invention relates to a process for manufacturing molecules comprising starting from a triazole alkyne of formula (IV), and carrying out the reaction of the compound (IV) with an azide.

Synthesis of Di-Triazoles

According to a first embodiment, the invention relates to a process for manufacturing a di-triazole of formula (V):

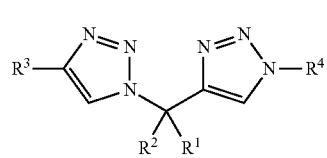

(V)

comprising starting from a triazole alkyne of formula (IV):

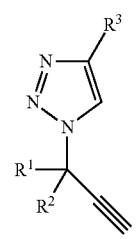

(IV)

wherein R¹ and R² are each independent groups as previously disclosed; or R¹ and R² form together a group as previously disclosed; and R³ is as previously disclosed; and from an azide of formula R⁴—N₃, wherein R⁴ is any R³ group as previously disclosed; and carrying out the reaction of compound (IV) with azide R⁴—N₃ in the presence of a copper(I) source.

This process is schematically represented below:

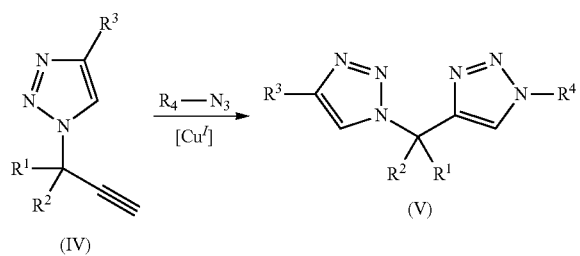

In this first embodiment, the compounds and the conditions of the step of reaction of compound (IV) with azide R⁴—N₃ may be as previously disclosed in any embodiment of previous paragraph entitled "CuAAC reaction —Alpha hydroxy-beta-triazolo-tetrazoles", except that the presence of a tertiary amine ligand may not be required.

According to a specific embodiment, $R^4$ is a carbohydrate.

According to a specific embodiment, $R^4$ is a metal complex.

According to a specific embodiment, $R^4$ is an alkyl or alkylaryl group optionally substituted by at least one group being alkyl, oxo, hydroxyl, tetrazolyl or halo and optionally interrupted or terminated by at least one group being —O— or —NH—.

According to a more specific embodiment, the di-triazoles manufactured by this process are selected from the group consisting of:
1-octyl-4-(1-(4-phenyl-1H-1,2,3-triazol-1-yl)cyclohexyl)-1H-1,2,3-triazole;
1-[bis(η5-cyclopentadienyl)iron]-4-(1-(4-phenyl-1H-1,2,3-triazol-1-yl)cyclohexyl)-1H-1,2,3-triazole;
2-(acetoxymethyl)-6-(4-(1-(4-phenyl-1H-1,2,3-triazol-1-yl)cyclohexyl)-1H-1,2,3-triazol-1-yl)tetrahydro-2H-pyran-3,4,5-triyl triacetate;
methyl 2-((tert-butoxycarbonyl)amino)-3-(4-(1-(4-phenyl-1H-1,2,3-triazol-1-yl)cyclohexyl)-1H-1,2,3-triazol-1-yl)propanoate;
1-octyl-4-(1-(4-phenyl-1H-1,2,3-triazol-1-yl)cyclooctyl)-1H-1,2,3-triazole;
ethyl 4-(4-(1-(4-phenyl-1H-1,2,3-triazol-1-yl)cyclooctyl)-1H-1,2,3-triazol-1-yl)butanoate;
4-phenyl-1-(1-(1-(pyren-1-ylmethyl)-1H-1,2,3-triazol-4-yl)cyclooctyl)-1H-1,2,3-triazole;
1-benzyl-4-(1-(4-phenyl-1H-1,2,3-triazol-1-yl)cyclooctyl)-1H-1,2,3-triazole;
2-ethyl-2-(4-(1-(4-phenyl-1H-1,2,3-triazol-1-yl)cyclooctyl)-1H-1,2,3-triazol-1-yl)-1-(1H-tetrazol-5-yl)butan-1-ol.

Synthesis of Poly-Triazoles

According to a second embodiment, the invention relates to a process for manufacturing an alpha-hydroxy-tetrazole of formula (VI):

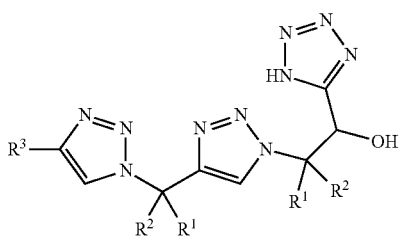
(VI)

comprising starting from a triazole alkyne of formula (IV):

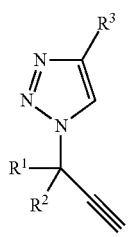
(IV)

and from an alpha-hydroxy-beta-azido tetrazole of formula (I):

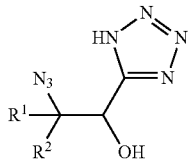
(I)

wherein $R^1$ and $R^2$ are each independent groups as previously disclosed; or $R^1$ and $R^2$ form together a group as previously disclosed; and $R_3$ is as previously disclosed;
and carrying out the reaction of the compound (IV) with compound (I) in presence of a copper(I) source and a tertiary amine.

According to a third embodiment, the invention relates to a process for manufacturing a poly-triazole compound of formula (VII):

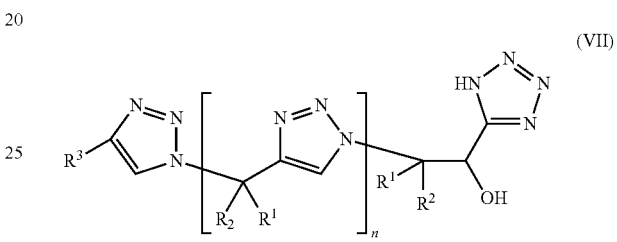
(VII)

comprising starting from a triazole alkyne of formula (IV):

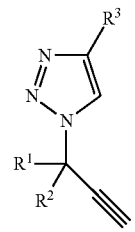
(IV)

and from an alpha-hydroxy-beta-azido tetrazole of formula (I):

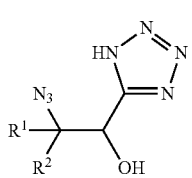
(I)

wherein $R^1$ and $R^2$ are each independent groups as previously disclosed; or $R^1$ and $R^2$ form together a group as previously disclosed; and $R_3$ is as previously disclosed;
and performing n iterations of the following steps (a) and (b):
(a) carrying out the reaction of the compound (IV) with compound (I) in the presence of a copper(I) source and a tertiary amine.
(b) carrying out the reaction of resulting compound with a carbodiimide.

This process is schematically represented below (L referring to the tertiary amine):

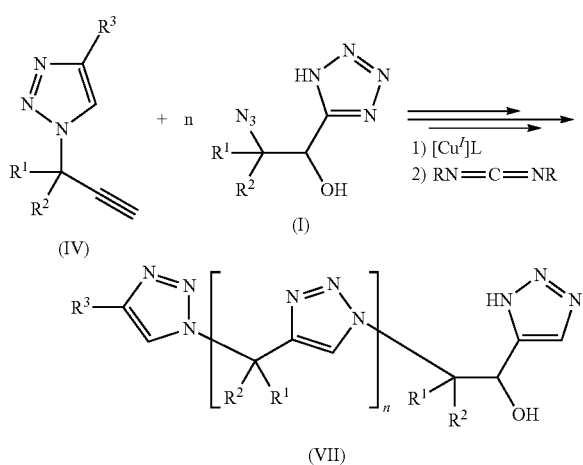

According to a specific embodiment, n ranges from 0 to 100. According to a more specific embodiment, n ranges from 1 to 10. According to another more specific embodiment, n ranges from 2 to 5.

According to a more specific embodiment, the polytriazoles manufactured by this process are selected from the group consisting in: 1-(3-ethylpent-1-yn-3-yl)-4-(1-(4-phenyl-1H-1,2,3-triazol-1-yl)cyclooctyl)-1H-1,2,3-triazole; 1-(1-ethynylcyclooctyl)-4-(3-(4-(1-(4-phenyl-1H-1,2,3-triazol-1-yl)cyclooctyl)-1H-1,2,3-triazol-1-yl)pentan-3-yl)-1H-1,2,3-triazole; and 1-benzyl-4-(1-(4-(3-(4-(1-(4-phenyl-1H-1,2,3-triazol-1-yl)cyclooctyl)-1H-1,2,3-triazol-1-yl)pentan-3-yl)-1H-1,2,3-triazol-1-yl)cyclooctyl)-1H-1,2,3-triazole.

In these second and third embodiments, the compounds and the conditions of step (a) may be as previously disclosed in any embodiment of previous paragraph entitled "CuAAC reaction —Alpha hydroxy-beta-triazolo-tetrazoles".

In this third embodiment, the compounds and the conditions of steps (b) may be as previously disclosed in any embodiment of previous paragraph entitled "Triazole alkynes —Hydroxy-tetrazole to alkyne reaction".

The triazole heterocycle is an analogue of the peptidic bound, therefore oligomeric or polymeric compounds of general formula (VII) are peptides analogues. Such biomimetic compounds may thus present valuable applications in medicinal chemistry, and more generally in the biotechnologies field.

EXAMPLES

The present invention is further illustrated by the following examples.

General Materials and Methods

Materials

Starting aldehydes, alkynes and ketones are commercially available from ordinary chemical compounds suppliers, and were purchased from Sigma-Aldrich, Alfa Aesar, Acros Organics or TCI Chemicals.

Azides were prepared using known methods of the literature: Octyl azide (*Org. Biomol. Chem.*, 2012, 10, 5993-6002), Ferrocenyl azide (*J. Organometal. Chem.*, 1970, 23, 225-228), Pyrene azide (J. Org. Chem. 2008, 73, 8212-8218), Methyl 3-azido-2-(tertbutoxycarbonyl-amino)propanoate (*Bioorg. Med. Chem.*, 2010, 18, 7338-7347), 2,3,4,6-Tetra-O-acetyl-1-azido-β-D-glucopyranoside (*Tet. Lett.* 2007 48 3953-3957), Ethyl 4-azido-butyrate (*Eur. J. Org. Chem.*, 2011, 229-233.). Benzyl azide was purchased from Sigma-Aldrich.

Other reactants and solvent are commercially available from ordinary chemical compounds suppliers, and were purchased from Sigma-Aldrich, Alfa Aesar, Acros Organics or TCI Chemicals.

Methods

Column chromatography were performed on a silica gel 230-400 mesh by using various mixtures of dichloromethane (DCM), ethyl acetate (EtOAc), methanol (MeOH), acetic acid (AcOH) and petroleum ether (PE). Thin Layer chromatographies (TLCs) were run on Kieselgel 60F$_{254}$ plates and revealed by UV light and potassium permanganate (epoxides) or ninhydrin (azido tetrazoles).

$^1$H and $^{13}$C NMR spectra were collected on a Bruker Avance spectrometer respectively at 200 or 300 MHz and 75 MHz. Data are presented as follows: chemical shift (in ppm on the δ scale relative to δTMS=0), multiplicity (s=singlet, d=doublet, t=triplet, m=multiplet, b=broad), coupling constant (J/Hz), integration and attribution. High resolution mass spectra (HR-MS) were obtained on a Waters Micromass Q-TofMicro instrument. Melting points are uncorrected.

Example 1: Epoxynitriles

Hereafter are provided epoxynitriles according to the invention. R$^1$ and R$^2$ groups refer to formula (II):

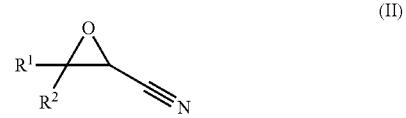

| # | R$^1$ | R$^2$ | Formula | Name |
|---|---|---|---|---|
| 1 | Ph | H | | trans-3-phenyloxirane-2-carbonitrile |
| 2 | Ph | H | | cis-3-phenyloxirane-2-carbonitrile |

-continued

| # | R¹ | R² | Formula | Name |
|---|---|---|---|---|
| 3 | naphthaen-2-yl | H | | trans-3-(naphthalen-2-yl)oxirane-2-carbonitrile |
| 4 | naphthaen-2-yl | H | | cis-3-(naphthalen-2-yl)oxirane-2-carbonitrile |
| 5 | 4-chlorophenyl | H | | trans-3-(4-chlorophenyl)oxirane-2-carbonitrile |
| 6 | 4-chlorophenyl | H | | cis-3-(4-chlorophenyl)oxirane-2-carbonitrile |
| 7 | thiophenyl | H | | 3-(thiophen-2-yl)oxirane-2-carbonitrile |
| 8 | styryl | H | | 3-styryloxirane-2-carbonitrile |
| 9 | heptyl | H | | 3-heptyloxirane-2-carbonitrile |
| 10 | Et | Et | | 3,3-diethyloxirane-2-carbonitrile |
| 11 | butyl | (cyclopentyl) | | 1-oxaspiro[2.4]heptane-2-carbonitrile |
| 12 | pentyl | (cyclohexyl) | | 1-oxaspiro[2.5]octane-2-carbonitrile |
| 13 | hexyl | (cycloheptyl) | | 1-oxaspiro[2.6]nonane-2-carbonitrile |
| 14 | heptyl | (cyclooctyl) | | 1-oxaspiro[2.7]decane-2-carbonitrile |

-continued

| # | R¹ | R² | Formula | Name |
|---|----|----|---------|------|
| 15 | Ph | Ph | | 3,3-diphenyloxirane-2-carbonitrile |
| 16 | fluorenyl | | | spiro[fluorene-9,2'-oxirane]-3'-carbonitrile |

These compounds may be prepared as disclosed in Example 2.

Example 2: Synthesis of epoxynitriles

Materials and Methods

Procedure (a) for the Synthesis of Epoxynitriles:

A solution of starting aldehyde or ketone (1 mol equiv.) and chloroacetonitrile (1.2 equiv.) in THF (15 mL/10 mmol) was added dropwise to a suspension of freshly crushed NaOH (3 equiv.) in THF (5 mL/10 mmol of NaOH). The reaction was stirred at room temperature and followed by TLC until full conversion of the aldehyde or ketone. Water (100 mL) and dichloromethane (100 mL) were added to the reaction mixture and the organic layer was washed with brine. The organic layer was concentrated under reduced pressure and the crude residue was purified by flash chromatography on silica gel or alumina.

Results

Hereafter are provided the yield and physical characterization of epoxynitriles #1-16 according to the invention, prepared from the appropriate aldehyde or ketone, by the above procedure.

| # | Name | Characterization | Yield |
|---|------|------------------|-------|
| 1 | trans-3-phenyloxirane-2-carbonitrile | $^1$H NMR (200 MHz, CDCl$_3$) δ 7.45-7.40 (m, 3H), 7.35-7.25 (m, 2H), 4.30 (d, J = 1.8 Hz, 1H), 3.43 (d, J = 1.8 Hz, 1H). $^{13}$C NMR (75 MHz, CDCl$_3$) δ132.75, 129.84, 128.99, 125.66, 116.03, 58.49, 44.64. HRMS (ESI, TOF MS) m/z calculated for [M + Na]+: 168.0426, found: 168.0427. | 29% |
| 2 | cis-3-phenyloxirane-2-carbonitrile | $^1$H NMR (200 MHz, CDCl$_3$) δ 7.50-7.35 (m, 5H), 4.26 (d, J = 3.7 Hz, 1H), 3.79 (d, J = 3.7 Hz, 1H). $^{13}$C NMR (75 MHz, CDCl$_3$) δ131.41, 129.73, 128.70, 126.32, 115.07, 57.72, 45.12. HRMS (ESI, TOF MS) m/z calculated for [M + Na]+: 168.0426, found: 168.0427. | 32% |
| 3 | trans-3-(naphthalen-2-yl)oxirane-2-carbonitrile | $^1$H NMR (200 MHz, CDCl$_3$) δ 7.95-7.80 (m, 4H), 7.60-7.50 (m, 2H), 7.35-7.25 (m, 1H), 4.46 (d, J = 1.7 Hz, 1H), 3.52 (d, J = 1.7 Hz, 1H). $^{13}$C NMR (75 MHz, CDCl$_3$) δ 133.87, 132.93, 130.04, 129.09, 127.98, 127.91, 127.08, 126.98, 126.15, 121.84, 116.06, 58.79, 44.71. HRMS (ESI, TOF MS) m/z calculated for [M + H]+: 196.0762, found: 196.0759. | 32% |
| 4 | cis-3-(naphthalen-2-yl)oxirane-2-carbonitrile | $^1$H NMR (200 MHz, CDCl$_3$) δ 7.80-7.00 (m, 4H), 7.65-7.45 (m, 3H), 4.43 (d, J = 3.7 Hz, 1H), 3.87 (d, J = 3.7 Hz, 1H).$^{13}$C NMR (75 MHz, CDCl$_3$) δ 133.89, 132.88, 128.81, 128.70, 128.18, 127.90, 126.93, 126.76, 126.31, 122.99, 115.06, 57.96, 45.28. HRMS (ESI, TOF MS) m/z calculated for [M + H]+: 196.0762, found: 196.0759. | 33% |
| 5 | trans-3-(4-chlorophenyl)oxirane-2-carbonitrile | $^1$H NMR (200 MHz, CDCl$_3$) δ 7.39 (d, J = 8.5 Hz, 2H), 7.23 (d, J = 8.5 Hz, 2H), 4.29 (d, J = 1.7 Hz, 1H), 3.41 (d, J = 1.7 Hz, 1H). $^{13}$C NMR (75 MHz, CDCl3) δ 135.85, 131.26, 129.28, 127.01, 115.73, 57.89, 44.66. HRMS (ESI, TOF MS): not detected. | 14% |
| 6 | cis-3-(4-chlorophenyl)oxirane-2-carbonitrile | $^1$H NMR (200 MHz, CDCl$_3$) δ 7.43 (d, J = 8.6 Hz, 2H) 7.37 (d, J = 8.6 Hz, 2H), 4.25 (d, J = 3.7 Hz, 1H), 3.80 (d, J = 3.7 Hz, 1H). $^{13}$C NMR (75 MHz, CDCl$_3$) δ 135.74, 129.96, 129.02, 127.71, 114.84, 57.14, 45.11. HRMS (ESI, TOF MS): not detected. | 28% |

-continued

| # | Name | Characterization | Yield |
|---|------|------------------|-------|
| 7 | 3-(thiophen-2-yl)oxirane-2-carbonitrile | $^1$H NMR (200 MHz, CDCl$_3$) δ 7.40 (dd, J = 5.0, 1.2 Hz, 1H$_{cis}$), 7.36 (dd, J = 5.0, 0.9 Hz, 1H$_{trans}$), 7.29 (dd, J = 2.4, 1.9 Hz, 1H$_{cis}$), 7.22 (dd, J = 3.6, 0.8 Hz, 1H$_{trans}$), 7.08 (dd, J = 5.4, 4.0 Hz, 1H$_{cis}$), 7.04 (dd, J = 5.0, 3.6 Hz, 1H$_{trans}$), 4.54 (d, J = 1.8 Hz, 1H$_{trans}$), 4.45 (d, J = 3.5 Hz, 1H$_{cis}$), 3.82 (d, J = 3.5 Hz, 1H$_{cis}$), 3.61 (d, J = 1.8 Hz, 1H$_{trans}$). $^{13}$C NMR (75 MHz, CDCl$_3$) δ 135.86 (trans), 134.20 (cis), 128.26 (trans), 127.75 (cis), 127.61 (trans), 127.45(cis), 127.10 (cis), 127.03 (trans), 115.63 (trans), 115.12 (cis), 55.59 (trans), 54.89 (cis), 45.82 (cis), 45.43(trans). HRMS (ESI, TOF MS) m/z calculated for [M + H]$^+$: 152.0170, found: 152.0172. | 89% |
| 8 | 3-styryloxirane-2-carbonitrile | Trans stereoisomer: $^1$H NMR (300 MHz, CDCl$_3$) δ 7.26 (m, 5H), 6.81 (d, J = 16.0 Hz, 1H), 5.67 (dd, J = 16.0, 7.8 Hz, 1H), 3.83 (dd, J = 7.8, 1.7 Hz, 1H), 3.32 (d, J = 1.8 Hz, 1H). $^{13}$C NMR (75 MHz, CDCl$_3$) δ 138.21, 134.98, 129.13, 128.89, 126.84, 121.49, 116.20, 58.94, 43.31.<br>Cis stereoisomer: $^1$H NMR (300 MHz, CDCl$_3$) δ 7.33 (m, 5H), 6.92 (d, J = 15.9 Hz, 1H), 5.98 (dd, J = 15.9, 8.1 Hz, 1H), 3.76 (dd, J = 8.1, 3.7 Hz, 1H), 3.65 (d, J = 3.7 Hz, 1H). $^{13}$C NMR (75 MHz, CDCl$_3$) δ 139.42, 135.04, 129.12, 128.82, 126.97, 120.30, 115.54, 57.54, 43.64.<br>HRMS (ESI, TOF MS) m/z calculated for [M + H]$^+$: 172.0762, found: 172.0763. | 31% |
| 9 | 3-heptyloxirane-2-carbonitrile | Trans stereoisomer: $^1$H NMR (300 MHz, CDCl$_3$) δ 3.34 (td, J = 6.0, 1.9 Hz, 1H), 3.17 (d, J = 1.9 Hz, 1H), 1.71-1.20 (m, 12H), 0.89 (t, J = 6.5 Hz, 3H). $^{13}$C NMR (75 MHz, CDCl$_3$) δ 116.80, 59.17, 40.95, 31.63, 31.01, 29.08, 29.02, 25.26, 22.57, 14.04.<br>Cis stereoisomer: $^1$H NMR (300 MHz, CDCl$_3$) δ 3.46 (d, J = 3.8 Hz, 1H), 3.19 (td, J = 6.0, 3.7 Hz, 1H), 1.88-1.17 (m, 12H), 0.90 (t, J = 6.6 Hz, 3H).$^{13}$C NMR (75 MHz, CDCl$_3$) δ 115.94, 57.44, 41.74, 31.66, 29.75, 29.15, 29.06, 25.72, 22.59, 14.07.<br>HRMS (ESI, TOF MS) m/z calculated for [M + H]$^+$: 168.1388, found: 168.1387. | 59% |
| 10 | 3,3-diethyloxirane-2-carbonitrile | $^1$H NMR (300 MHz, CDCl$_3$) δ 3.27 (s, 1H), 1.96-1.62 (m, 4H), 1.09 (td, J = 7.5, 1.3 Hz, 3H), 0.92 (td, J = 7.5, 1.3 Hz, 3H). $^{13}$C NMR (75 MHz, CDCl$_3$) δ 116.48, 67.34, 46.21, 25.44, 25.12, 9.07, 8.31. HRMS (ESI, TOF MS) m/z calculated for [M + H]$^+$: 126.0919, found: 126.0917. | 55% |
| 11 | 1-oxaspiro[2.4]heptane-2-carbonitrile | $^1$H NMR (300 MHz, CDCl$_3$) δ 3.46 (s, 1H), 2.17-1.60 (m, 8H). $^{13}$C NMR (75 MHz, CDCl$_3$) δ 116.59, 71.43, 45.78, 31.84, 30.62, 25.33, 24.92. HRMS (ESI, TOF MS) m/z calculated for [M + H]$^+$: 124.0762, found: 124.0766. | 82% |
| 12 | 1-oxaspiro[2.5]octane-2-carbonitrile | $^1$H NMR (300 MHz, CDCl$_3$) δ 3.24 (s, 1H), 1.83-1.49 (m, 10H). $^{13}$C NMR (75 MHz, CDCl$_3$) δ 116.27, 65.46, 47.39, 33.17, 31.07, 24.75, 24.58. HRMS (ESI, TOF MS) m/z calculated for [M + H]$^+$: 138.0919, found: 138.0913 | 86% |
| 13 | 1-oxaspiro[2.6]nonane-2-carbonitrile | $^1$H NMR (300 MHz, CDCl$_3$) δ 3.25 (s, 1H), 2.12-1.44 (m, 12H). $^{13}$C NMR (75 MHz, CDCl$_3$) δ 116.46, 66.79, 48.58, 35.46, 33.17, 28.84, 28.68, 24.33, 23.99.IR (cm$^{-1}$) ν$_{max}$: 2930, 2859, 2244, 1468, 1448, 943. HRMS (ESI, TOF MS) m/z calculated for [M + H]$^+$: 152.1075, found: 152.1071. | 85% |
| 14 | 1-oxaspiro[2.7]decane-2-carbonitrile | $^1$H NMR (300 MHz, CDCl$_3$) δ 3.28 (s, 1H), 2.01-1.46 (m, 14H). $^{13}$C NMR (75 MHz, CDCl$_3$) δ 116.50, 66.29, 49.11, 33.76, 31.74, 26.45, 25.89, 24.96, 24.35, 22.69. HRMS (ESI, TOF MS) m/z calculated for [M + H]$^+$: 166.1232, found: 166.1233. | 48% |
| 15 | 3,3-diphenyloxirane-2-carbonitrile | Mp: 75° C. $^1$H NMR (300 MHz, CDCl$_3$) δ 7.41-7.21 (m, 10H), 3.83 (s, 1H). $^{13}$C NMR (75 MHz, CDCl$_3$) δ 136.44, 134.48, 129.34, 129.32, 128.81, 128.65, 127.72, 127.34, 115.27, 67.68, 50.11. HRMS (ESI, TOF MS) m/z calculated for [M + H]$^+$: 222.0919, found: 222.0919. | 88% |
| 16 | spiro[fluorene-9,2'-oxirane]-3'-carbonitrile | Mp: 122° C. $^1$H NMR (300 MHz, CDCl$_3$) δ 7.65-7.02 (m, 8H), 4.12 (s, 1H). $^{13}$C NMR (75 MHz, CDCl$_3$) δ 141.57, 141.35, 137.30, 135.48, 130.86, 130.78, 128.15, 127.99, 123.78, 121.55, 120.82, 120.78, 115.17, 67.20, 48.31. HRMS (ESI, TOF MS) m/z calculated for [M + H]$^+$: 220.0762, found: 220.0759. | 42% |

Example 3: Alpha-Hydroxy-Beta-Azido Tetrazoles

Hereafter are provided alpha-hydroxy-beta-azido tetrazoles according to the invention. $R^1$ and $R^2$ groups refer to formula (I):

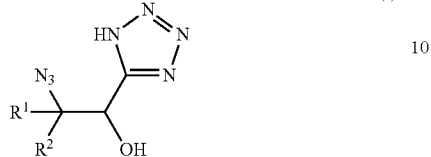

(I)

| # | $R^1$ | $R^2$ | Formula | Name |
|---|---|---|---|---|
| 17 | Ph | H | | anti-2-azido-2-phenyl-1-(1H-tetrazol-5-yl)ethan-1-ol |
| 18 | Ph | H | | syn-2-azido-2-phenyl-1-(1H-tetrazol-5-yl)ethan-1-ol |
| 19 | naphthalen-2-yl | H | | anti-2-azido-2-(naphthalen-2-yl)-1-(1H-tetrazol-5-yl)ethan-1-ol |
| 20 | naphthalen-2-yl | H | | syn-2-azido-2-(naphthalen-2-yl)-1-(1H-tetrazol-5-yl)ethan-1-ol |
| 21 | 4-chlorophenyl | H | | anti-2-azido-2-(4-chlorophenyl)-1-(1H-tetrazol-5-yl)ethan-1-ol |
| 22 | 4-chlorophenyl | H | | syn-2-azido-2-(4-chlorophenyl)-1-(1H-tetrazol-5-yl)ethan-1-ol |
| 23 | thiophenyl | H | | 2-azido-1-(1H-tetrazol-5-yl)-2-(thiophen-2-yl)ethan-1-ol |

-continued

| # | R¹ | R² | Formula | Name |
|---|---|---|---|---|
| 24 | styryl | H | | (E)-2-azido-4-phenyl-1-(1H-tetrazol-5-yl)but-3-en-1-ol |
| 25 | heptyl | H | | 2-azido-1-(1H-tetrazol-5-yl)nonan-1-ol |
| 26 | Et | Et | | 2-azido-2-ethyl-1-(1H-tetrazol-5-yl)butan-1-ol |
| 27 | butyl (cyclopentyl) | | | (1-azidocyclopentyl)(1H-tetrazol-5-yl)methanol |
| 28 | pentyl (cyclohexyl) | | | (1-azidocyclohexyl)(1H-tetrazol-5-yl)methanol |
| 29 | hexyl (cycloheptyl) | | | (1-azidocycloheptyl)(1H-tetrazol-5-yl)methanol |
| 30 | heptyl (cyclooctyl) | | | (1-azidocyclooctyl)(1H-tetrazol-5-yl)methanol |
| 31 | Ph | Ph | | 2-azido-2,2-diphenyl-1-(1H-tetrazol-5-yl)ethan-1-ol |

| # | R¹ | R² | Formula | Name |
|---|---|---|---|---|
| 32 | fluorenyl | | (structure: 9-fluorenyl with N₃ and CH(OH)-tetrazole substituents) | (9-azido-9H-fluoren-9-yl)(1H-tetrazol-5-yl)methanol |

These compounds may be prepared as disclosed in Example 4.

Example 4: Synthesis of Alpha-Hydroxy-Beta-Azido-Tetrazoles

Materials and Methods
Procedure (b) for the Synthesis of Alpha-Hydroxy-Beta-Azido-Tetrazoles A solution of epoxynitrile (1 equiv.), $Bu_2SnO$ (0.5 equiv.) and $TMSN_3$ (3 equiv.) in toluene (10 mL/mmol of epoxide) was stirred at 60° C. for 18 h. The solvent was removed under reduced pressure and a 1:1 THF/2N aqueous HCl mixture (20 mL) was added to the crude and stirred for 30 min Water and EtOAc were added and the aqueous layer was extracted (EtOAc), washed with brine and dried over $MgSO_4$. Evaporation gave a residue that was washed by trituration with small portions of dichloromethane. Further purification could be done by flash chromatography over silica gel using dichloromethane/MeOH/Acetic acid: 9/0.5/0.5 mixture as eluent (spots were revealed with ninhydrin).

Results

Hereafter are provided the yield and physical characterization of alpha-hydroxy-beta-azido tetrazoles according to the invention, prepared by the above procedure.

Compounds #17-32 were respectively prepared from epoxynitriles #1-16 disclosed in Examples 1 and 2.

| # | Name | Characterization | Yield |
|---|---|---|---|
| 17 | anti-2-azido-2-phenyl-1-(1H-tetrazol-5-yl)ethan-1-ol | Mp: 175° C. ¹H NMR (300 MHz, DMSO) δ 7.40-7.20 (m, 5H), 6.76 (dl, J = 4.9 Hz, 1H), 5.33 (t, J = 5.3 Hz, 1H), 5.16 (d, J = 6.0 Hz, 1H). ¹³C NMR (75 MHz, DMSO) δ 156.76, 135.34, 128.31, 127.85, 67.58, 67.39. HRMS (ESI, TOF MS) m/z calculated for [M + H]⁺: 232.0947, found: 232.0950. | 85% |
| 18 | syn-2-azido-2-phenyl-1-(1H-tetrazol-5-yl)ethan-1-ol | Mp: 176° C. ¹H NMR (300 MHz, DMSO) δ 7.35-7.20 (m, 5H), 6.88 (dl, J = 5.8 Hz, 1H), 5.28 (t, J = 5.6 Hz, 1H), 5.07 (d, 1H, J = 6.1 Hz). ¹³C NMR (75 MHz, DMSO) δ 135.71, 128.49, 127.89, 68.13, 68.05. HRMS (ESI, TOF MS) m/z calculated for [M + H]⁺: 232.0947, found: 232.0950. | 65% |
| 19 | anti-2-azido-2-(naphthalen-2-yl)-1-(1H-tetrazol-5-yl)ethan-1-ol | Mp: 211° C. (dec.). ¹H NMR (300 MHz, DMSO) δ 8.00-7.85 (m, 3H), 7.82 (s, 1H), 7.60-7.45 (m, 2H), 7.42 (d, 1H, J = 8.6 Hz), 6.83 (dl, J = 4.7 Hz, 1H), 5.45 (t, J = 5.0 Hz, 1H), 5.36 (d, J = 5.9 Hz, 1H). ¹³C NMR (75 MHz, DMSO) δ 132.95, 132.66, 132.44, 127.92, 127.50, 127.17, 126.42, 126.36, 125.31, 67.78, 67.47. HRMS (ESI, TOF MS) m/z calculated for [M + H]⁺: 282.1103, found: 282.1101. | 55% |
| 20 | syn-2-azido-2-(naphthalen-2-yl)-1-(1H-tetrazol-5-yl)ethan-1-ol | Mp: 209° C. (dec.). ¹H NMR (300 MHz, DMSO) δ 7.90-7.80 (m, 4H), 7.60-7.40 (m, 4H), 5.41 (d, J = 6.4 Hz, 1H), 5.36 (d, J = 6.4 Hz, 1H). ¹³C NMR (75 MHz, DMSO) δ 133,26,64, 132.44, 128.02, 127.91, 127.51, 127.05, 126.46, 126.39, 125.35, 68.35, 68.11. HRMS (ESI, TOF MS) m/z calculated for [M + H]⁺: 282.1103, found: 282.1101. | 56% |
| 21 | anti-2-azido-2-(4-chlorophenyl)-1-(1H-tetrazol-5-yl)ethan-1-ol | Mp: 198° C. (dec.). ¹H NMR (300 MHz, DMSO) δ 7.40 (d, J = 8.5 Hz, 2H), 7.28 (d, J = 8.5 Hz, 2H), 6.82 (dl, J = 3.2 Hz, 1H), 5.34 (t, J = 4.9 Hz, 1H), 5.22 (d, J = 5.7 Hz, 1H). ¹³C NMR (75 MHz, DMSO) δ 134.36, 132.93, 129.72, 128.27, 67.43, 66.75. HRMS (ESI, TOF MS) m/z calculated for [M + H]⁺: 266.0560, found: 266.0557. | 63% |
| 22 | syn-2-azido-2-(4-chlorophenyl)-1-(1H-tetrazol-5-yl)ethan-1-ol | Mp: 203° C. (dec.). ¹H NMR (300 MHz, DMSO) δ 7.42 (d, J = 8.6 Hz, 2H), 7.34 (d, J = 8.6 Hz, 2H), 6.91 (dl, J = 5.5 Hz, 1H), 5.29 (t, J = 5.3 Hz, 1H), 5.14 (d, J = 6.0 Hz, 1H). ¹³C NMR (75 MHz, DMSO) δ 134.73, 133.03, 129.74, 128.39, 67.93, 67.18. HRMS (ESI, TOF MS) m/z calculated for [M + H]⁺: 266.0560, found: 266.0557. | 51% |

-continued

| # | Name | Characterization | Yield |
|---|------|------------------|-------|
| 23 | 2-azido-1-(1H-tetrazol-5-yl)-2-(thiophen-2-yl)ethan-1-ol | Mp: 125° C. $^1$H NMR (300 MHz, DMSO) δ 7.57 (d, J = 5.1 Hz, 1H$_{min}$), 7.51 (d, J = 5.1 Hz, 1H$_{maj}$), 7.19 (d, J = 2.8 Hz, 1H$_{min}$), 7.12 (d, J = 2.8 Hz, 1H$_{maj}$), 7.07 (s, 1H), 7.03 (dd, J = 5.1, 3.6 Hz, 1H$_{min}$), 6.99 (dd, J = 5.0, 3.6 Hz, 1H$_{maj}$), 5.45 (d, J = 4.8 Hz, 1H$_{maj}$), 5.36 (d, J = 4.5 Hz, 1H$_{maj}$ + 1H$_{min}$), 5.32 (d, J = 4.3 Hz, 1H$_{min}$). $^{13}$C NMR (75 MHz, DMSO) δ 156.94 (maj), 156.21 (min), 137.18 (min), 136.35 (maj), 128.00 (maj), 127.84 (min), 127.34 (min), 127.23 (maj), 126.51 (min), 67.93 (min), 67.54 (maj), 63.35 (min), 63.32 (maj). HRMS (ESI, TOF MS) m/z calculated for [M + H]$^+$: 238.0511, found: 238.0514. | 38% |
| 24 | (E)-2-azido-4-phenyl-1-(1H-tetrazol-5-yl)but-3-en-1-ol | Mp: 134° C. $^1$H NMR (300 MHz, DMSO) δ 7.52-7.23 (m, 5H), 6.85 (s, 1H), 6.81 (d, J = 16.0 Hz, 1H$_{min}$), 6.69 (d, J = 15.9 Hz, 1H$_{maj}$), 6.38 (dd, J = 15.9, 8.0 Hz, 1H$_{min}$), 6.31 (dd, J = 15.9, 8.0 Hz, 1H$_{maj}$), 5.25 (bm, 1H$_{min}$), 5.24 (bm, 1H$_{maj}$), 4.66 (dd, J = 7.5, 4.5 Hz, 1H$_{maj}$), 4.58 (dd, J = 7.8, 4.4 Hz, 1H$_{min}$). $^{13}$C NMR (75 MHz, DMSO) δ 156.33, 135.55 (min), 135.52 (maj), 135.07 (maj), 134.89 (min), 128.69 (maj), 128.29 (min), 126.63 (min), 126.58 (maj), 122.79 (min), 122.27 (maj), 67.34 (min), 67.08 (maj), 66.68 (maj), 66.51(min). HRMS (ESI, TOF MS) m/z calculated for [M + H]$^+$ : 258.1103, found: 258.1102. | 52% |
| 25 | 2-azido-1-(1H-tetrazol-5-yl)nonan-1-ol | Mp: 146° C. $^1$H NMR (300 MHz, DMSO) δ 6.69 (s, 1H), 5.15 (d, J = 3.9 Hz, 1H), 3.85-3.75 (m, 1H), 1.60-1.10 (m, 12H), 0.89-0.79 (m, 3H). $^{13}$C NMR (75 MHz, DMSO) δ 156.27, 67.31, 65.57, 31.10, 29.01, 28.56, 28.45, 25.51, 22.02, 13.88. HRMS (ESI, TOF MS) m/z calculated for [M + H]$^+$: 254.1729, found: 254.1732. | 70% |
| 26 | 2-azido-2-ethyl-1-(1H-tetrazol-5-yl)butan-1-ol | Mp: 128° C.$^1$H NMR (300 MHz, DMSO) δ 6.74 (d, J = 4.3 Hz, 1H), 5.10 (d, J = 4.2 Hz, 1H), 1.95-1.75 (m, 2H), 1.45-1.25 (m, 2H), 0.94 (t, J = 7.3 Hz, 3H), 0.80 (t, J = 7.3 Hz, 3H). $^{13}$C NMR (75 MHz, DMSO) δ 156.27, 68.60, 24.24, 23.04, 7.55, 7.36. HRMS (ESI, TOF MS) m/z calculated for [M + H]$^+$: 212.1260, found: 212.1262. | 60% |
| 27 | (1-azidocyclopentyl)(1H-tetrazol-5-yl)methanol | Mp: 161° C. $^1$H NMR (300 MHz, DMSO) δ 6.78 (d, J = 4.5 Hz, 1H), 5.10 (d, J = 4.4 Hz, 1H), 1.97-1.75 (m, 2H), 1.45-1.22 (m, 6H). $^{13}$C NMR (75 MHz, DMSO) δ 156.68, 75.15, 70.60, 33.55, 33.11, 23.41, 23.30. HRMS (ESI, TOF MS) m/z calculated for [M + H]$^+$: 210.1103, found: 210.1104. | 53% |
| 28 | (1-azidocyclohexyl)(1H-tetrazol-5-yl)methanol | Mp: 175° C. $^1$H NMR (300 MHz, DMSO) δ 6.80 (d, J = 4.8 Hz, 1H), 5.06 (d, J = 4.8 Hz, 1H), 2.23-0.91 (m, 10H). $^{13}$C NMR (75 MHz, DMSO) δ 156.01, 71.40, 65.48, 30.23, 29.77, 24.54, 21.39, 21.14. HRMS (ESI, TOF MS) m/z calculated for [M + H]$^+$: 224.1260, found: 224.1264. | 75% |
| 29 | (1-azidocycloheptyl)(1H-tetrazol-5-yl)methanol | Mp: 172° C. $^1$H NMR (300 MHz, DMSO) δ 6.81 (d, J = 4.8 Hz, 1H), 5.00 (d, J = 4.8 Hz, 1H), 2.19-1.04 (m, 12H). $^{13}$C NMR (75 MHz, DMSO) δ 156.21, 70.95, 68.96, 33.67, 33.07, 28.91, 28.88, 21.75, 21.66. HRMS (ESI, TOF MS) m/z calculated for [M + H]$^+$: 238.1416, found: 238.1408. | 76% |
| 30 | (1-azidocyclooctyl)(1H-tetrazol-5-yl)methanol | Mp: 186° C.$^1$H NMR (300 MHz, DMSO) δ 6.76 (d, J = 4.6 Hz, 1H), 5.06 (d, J = 4.6 Hz, 1H), 2.23-1.88 (m, 2H), 1.77-1.18 (m, 12H). $^{13}$C NMR (75 MHz, DMSO) δ 156.26, 70.09, 68.91, 29.79, 28.06, 27.71, 27.21, 24.10, 21.49, 21.26. HRMS (ESI, TOF MS) m/z calculated for [M + H]$^+$: 252.1573, found: 252.1576. | 51% |
| 31 | 2-azido-2,2-diphenyl-1-(1H-tetrazol-5-yl)ethan-1-ol | Mp: 205° C. $^1$H NMR (300 MHz, DMSO) δ 7.63-7.29 (m, 5H), 7.22-6.99 (m, 6H), 6.39 (d, J = 4.2 Hz, 1H). $^{13}$C NMR (75 MHz, DMSO) δ 155.27, 140.06, 128.56, 127.95, 127.93, 127.71, 127.25, 126.11, 74.31, 69.88. HRMS (ESI, TOF MS) m/z calculated for [M + H]$^+$: 308.1260, found: 308.1252. | 61% |
| 32 | (9-azido-9H-fluoren-9-yl)(1H-tetrazol-5-yl)methanol | Mp: 213° C. $^1$H NMR (300 MHz, DMSO) δ 7.82 (d, J = 6.9 Hz, 2H), 7.57-7.35 (m, 6H), 7.31 (d, J = 5.0 Hz, 1H), 5.68 (d, J = 4.8 Hz, 1H). $^{13}$C NMR (75 MHz, DMSO) δ 155.35, 141.47, 140.69, 140.13, 139.92, 129.87, 127.94, 127.81, 125.47, 125.14, 120.44, 74.21, 69.45. HRMS (ESI, TOF MS) m/z calculated for [M + H]$^+$: 306.1103, found: 306.1111. | 61% |

These results evidence that the applicant successfully conceived and reduced to practice an efficient, straightforward and stereospecific synthesis of alpha-hydroxy-beta-azido tetrazoles.

Various combinations of $R^1$ and $R^2$ substituting groups were used, confirming that the scope of procedure (b) is very broad.

Example 5: Alpha-Hydroxy-Beta-Triazolo-Tetrazoles

Hereafter are provided alpha-hydroxy-beta-triazolo-tetrazoles according to the invention. $R^1$, $R^2$ and $R^3$ groups refer to formula (III):

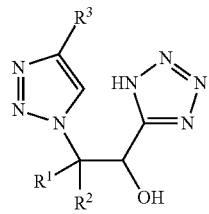

(III)

| # | $R^1$ | $R^2$ | $R^3$ | Formula | Name |
|---|---|---|---|---|---|
| 33 | pentyl (cyclohexyl) | | Ph | | (1-(4-phenyl-1H-1,2,3-triazol-1-yl)cyclohexyl)(1H-tetrazol-5-yl)methanol |
| 34 | hexyl (cycloheptyl) | | Ph | | (1-(4-pheny1-1H-1,2,3-triazol-1-yl)cycloheptyl)(1H-tetrazol-5-yl)methanol |
| 35 | heptyl (cyclooctyl) | | Ph | | (1-(4-phenyl-1H-1,2,3-triazol-1-yl)cyclooctyl)(1H-tetrazol-5-yl)methanol |
| 36 | heptyl (cyclooctyl) | | —COOtBu | | tert-butyl 1-(1-(hydroxy(1H-tetrazol-5-yl)methyl)cyclooctyl)-1H-1,2,3-triazole-4-carboxylate |

-continued

| # | R¹ | R² | R³ | Formula | Name |
|---|---|---|---|---|---|
| 37 | heptyl | (cyclooctyl) | 3-chloropropyl | | (1-(4-(3-chloropropyl)-1H-1,2,3-triazol-1-yl)cyclooctyl)(1H-tetrazol-5-yl)methanol |
| 38 | heptyl | (cyclooctyl) | 2-hydroxyethyl | | 2-(1-(1-(hydroxy(1H-tetrazol-5-yl)methyl)cyclooctyl)-1H-1,2,3-triazol-4-yl)ethan-1-ol |
| 39 | Et | Et | Ph | | 2-ethyl-2-(4-phenyl-1H-1,2,3-triazol-1-yl)-1-(1H-tetrazol-5-yl)butan-1-ol |
| 40 | Ph | H | hexyl | | 2-(4-hexyl-1H-1,2,3-triazol-1-yl)-2-phenyl-1-(1H-tetrazol-5-yl)ethan-1-ol |

-continued

| # | R¹ | R² | R³ | Formula | Name |
|---|----|----|----|---------|------|
| 41 | Ph | Ph | hexyl | 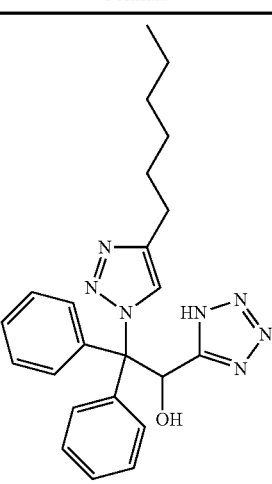 | 2-(4-hexyl-1H-1,2,3-triazol-1-yl)-2,2-diphenyl-1-(1H-tetrazol-5-yl)ethan-1-ol |
| 42 | Ph | Ph | 3-chloropropyl | 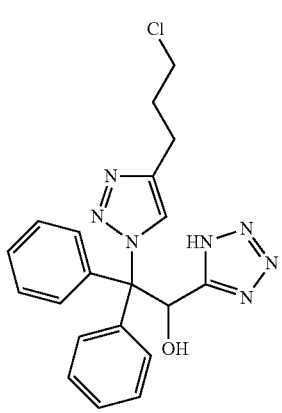 | 2-(4-(3-chloropropyl)-1H-1,2,3-triazol-1-yl)-2,2-diphenyl-1-(1H-tetrazol-5-yl)ethan-1-ol |
| 43 | Ph | Ph | —COOtBu | 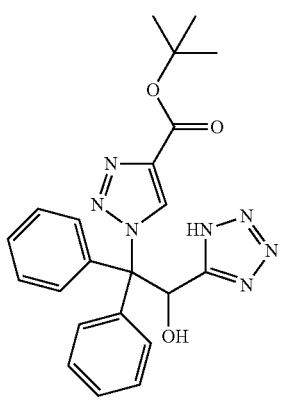 | tert-butyl 1-(2-hydroxy-1,1-diphenyl-2-(1H-tetrazol-5-yl)ethyl)-1H-1,2,3-triazole-4-carboxylate |

These compounds may be prepared as disclosed in Example 6.

Example 6: CuAAC Synthesis of Alpha-Hydroxy-Beta-Triazolo-Tetrazoles

Materials and Methods
Procedures for the Synthesis of Alpha-Hydroxy-Beta-Tetrazo-Tetrazoles
Procedure (c):
The alpha-hydroxy-beta-azido-tetrazole substrate (1 mmol) was dissolved in n-BuOH (3 mL). An alkyne (3 mmol) and TBTA (tris((1-benzyl-1H-1,2,3-triazolyl)methyl) amine) (0.1 mmol) were added. A solution of sodium ascorbate (0.2 mmol in 1.5 mL water) was added, followed by a solution of copper sulphate (0.1 mmol in 1.5 mL water). The mixture was stirred at room temperature for 48 hours. The organic phase was separated and concentrated under reduced pressure. The residue was purified by flash chromatography on silica gel.

Procedure (d):
A mixture of alpha-hydroxy-beta-azido-tetrazole substrate (0.10 mmol), copper (I) bromide (0.01 mmol) and TBTA (0.011 mmol) in THF (1 mL) was placed under argon atmosphere. An alkyne (0.30 mmol) and diisopropylethylamine (0.05 mL, 0.30 mmol) were added, and the mixture was stirred for 24 hours. The mixture was concentrated under reduced pressure. The residue was purified by flash chromatography on silica gel.

Results

Hereafter are provided the yield and physical characterization of alpha-hydroxy-beta-triazolo-tetrazoles according to the invention, prepared by procedure (c) above. Compound #35 was also prepared by procedure (d).

Compounds #33-43 were prepared from the corresponding alpha-hydroxy-beta-azido-tetrazoles disclosed in Example 3 and 4 and from the appropriate $R^3$—C≡CH terminal alkyne.

| # | Name | Characterization | Yield |
|---|------|-----------------|-------|
| 33 | (1-(4-phenyl-1H-1,2,3-triazol-1-yl)cyclohexyl)(1H-tetrazol-5-yl)methanol | Mp: 210-212° C. $^1$H NMR (300 MHz, DMSO-d6) δ 8.60 (s, 1H), 7.87 (m, 2H), 7.44 (m, 2H), 7.31 (m, 1H), 6.76 (d, J = 5.0 Hz, 1H), 5.15 (d, J = 5.0 Hz, 1H), 2.61-2.66 (m, 2H), 1.88-1.96 (m, 2H), 1.48-1.67 (m, 3H), 1.08-1.29 (m, 3H). $^{13}$C NMR (75 MHz, DMSO-d6) δ 155.9, 145.6, 131.1, 128.7, 127.6, 125.1, 121.5, 70.9, 66.3, 30.3, 24.3, 20.9, 20.8. HRMS (ESI, TOF MS) m/z calculated for $C_{16}H_{20}N_7O$ [M + H]$^+$: 326.1729, found: 326.1719. | 84% (c) |
| 34 | (1-(4-phenyl-1H-1,2,3-triazol-1-yl)cycloheptyl)(1H-tetrazol-5-yl)methanol | Mp: 119-120° C. $^1$H NMR (300 MHz, DMF-d6) δ 8.74 (s, 1H), 7.98 (m, 2H), 7.47 (m, 2H), 7.35 (m, 1H), 7.03 (bs, 1H), 5.46 (bs, 1H), 3.53 (bs, 1H), 2.32-2.36 (m, 2H), 1.88-1.96 (m, 2H), 1.45-1.54 (m, 8H). $^{13}$C NMR (75 MHz, DMF-d6) δ 147.3, 132.8, 130.0, 129.8, 128.6, 126.3, 122.6, 72.8, 71.9, 30.4, 23.2, 23.1, 21.7. HRMS (ESI, TOF MS) m/z calculated for $C_{17}H_{22}N_7O$ [M + H]$^+$: 340.1886, found: 340.1893. | 98% (c) |
| 35 | (1-(4-phenyl-1H-1,2,3-triazol-1-yl)cyclooctyl)(1H-tetrazol-5-yl)methanol | Mp: 86-88° C. $^1$H NMR (300 MHz, DMF-d6) δ 8.71 (s, 1H), 7.96 (m, 2H), 7.44-7.49 (m, 2H), 7.34 (m,, 1H), 7.03 (bs, 1H), 5.48 (s, 1H), 3.66 (bs, 1H), 2.52-2.72 (m, 3H), 2.36-2.43 (m, 1H), 1.47-1.77 (m, 12H). $^{13}$C NMR (75 MHz, DMF-d6) δ 157.7, 146.9, 132.8, 129.8, 128.6, 126.3, 122.7, 80.2, 71.7, 71.6, 29.3, 28.5, 25.7, 22.8. HRMS (ESI, TOF MS) m/z calculated for $C_{18}H_{24}N_7O$ [M + H]$^+$: 354.2042, found: 354.2045. | 98% (c) 90% (d) |
| 36 | tert-butyl 1-(1-(hydroxy(1H-tetrazol-5-yl)methyl)cyclooctyl)-1H-1,2,3-triazole-4-carboxylate | Mp: 118-120° C. $^1$H NMR (300 MHz, DMSO-d6) δ 8.60 (s, 1H), 6.83 (bs, 1H), 5.25 (s, 1H), 2.25-2.45 (m, 3H), 1.26-1.66 (m, 20H). $^{13}$C NMR (75 MHz, DMSO-d6) δ 159.9, 139.5, 128.9, 81.1, 69.8, 29.1, 27.9, 26.3, 24.2, 21.3. HRMS (ESI, TOF MS) m/z calculated for $C_{17}H_{28}N_7O_3$ [M + H]$^+$: 378.2254, found: 378.2257. | 98% (c) |
| 37 | (1-(4-(3-chloropropyl)-1H-1,2,3-triazol-1-yl)cyclooctyl)(1H-tetrazol-5-yl)methanol | Mp: 85-87° C. $^1$H NMR (300 MHz, CDCl$_3$) δ 7.23 (s, 1H), 5.51 (s, 1H), 3.45 (t, J = 5.9 Hz, 1H), 2.67-2.79 (m, 4H), 2.42-2.51 (m, 2H), 2.01-2.04 (m, 2H), 1.47-1.82 (m, 10H). $^{13}$C NMR (75 MHz, CDCl$_3$) δ 121.8, 72.1, 71.3, 43.7, 31.6, 30.4, 29.6, 28.2, 27.3, 24.9, 22.1, 22.0. HRMS (ESI, TOF MS) m/z calculated for $C_{15}H_{25}N_7OCl$ [M + H]$^+$: 354.1809, found: 354.1810. | 71% (c) |
| 38 | 2-(1-(1-(hydroxy(1H-tetrazol-5-yl)methyl)cyclooctyl)-1H-1,2,3-triazol-4-yl)ethan-1-ol | $^1$H NMR (300 MHz, CD$_3$OD) δ 7.87 (s, 1H), 5.28 (s, 1H), 3.83 (t, J = 6.7 Hz, 1H), 2.90 (t, J = 6.5 Hz, 1H), 2.30-2.61 (m, 4H), 1.43-1.57 (m, 10H). $^{13}$C NMR (75 MHz, CDCl$_3$) δ 158.7, 145.3, 124.4, 72.2, 72.0, 62.2, 30.9, 30.2, 30.0, 29.6, 28.8, 26.0, 23.1. HRMS (ESI, TOF MS) m/z calculated for $C_{14}H_{24}N_7O_2$ [M + H]$^+$: 322.1991, found: 322.1995. | 94% (c) |
| 39 | 2-ethyl-2-(4-phenyl-1H-1,2,3-triazol-1-yl)-1-(1H-tetrazol-5-yl)butan-1-ol | Mp: 103-105° C. $^1$H NMR (300 MHz, DMSO-d6) δ 8.56 (s, 1H), 7.87 (m, 2H), 7.43 (m,, 2H), 7.30 (m, 1H), 6.84 (d, J = 5.4 Hz, 1H), 5.34 (d, J = 5.4 Hz, 1H), 2.18-2.36 (m, 4H), 0.90 (t, J = 7.3 Hz, 3H), 0.83 (t, J = 7.4 Hz, 3H). $^{13}$C NMR (75 MHz, DMSO-d6) δ 156.2, 145.3, 131.1, 128.7, 127.6, 125.1, 121.5, 69.9, 68.3, 24.6, 23.8, 7.5. HRMS (ESI, TOF MS) m/z calculated for $C_{15}H_{20}N_7O$ [M + H]$^+$: 314.1729, found: 314.1724. | 99% (c) |
| 40 | 2-(4-hexyl-1H-1,2,3-triazol-1-yl)-2-phenyl-1-(1H-tetrazol-5-yl)ethan-1-ol | Mp: 157-159° C. $^1$H NMR (300 MHz, DMF-d6) δ 8.32 (bs, 1H), 7.30-7.53 (m, 5H), 6.37 (b, 2H), 2.66 (t, J = 7.3 Hz, 1H), 1.61-1.64 (m, 2H), 1.30 (b, 6H), 0.87 (t, J = 5.8 Hz, 1H). $^{13}$C NMR (75 MHz, DMF-d6) δ 136.7, 128.8, 128.3, 122.2, 68.6, 66.9, 31.7, 28.9, 25.7, 22.6, 13.8. HRMS (ESI, TOF MS) m/z calculated for $C_{17}H_{24}N_7O$ [M + H]$^+$: 342.2042, found: 342.2049. | 78% (c) |
| 41 | 2-(4-hexyl-1H-1,2,3-triazol-1-yl)-2,2-diphenyl-1-(1H-tetrazol-5-yl)ethan-1-ol | $^1$H NMR (300 MHz, CDCl$_3$) δ 7.21-7.38 (m, 10H), 6.82-6.93 (m, 3H), 2.63-2.65 (m, 1H), 1.57 (m, 2H), 1.26 (b, 6H), 0.85 (t, J = 5.8 Hz, 3H). $^{13}$C NMR (75 MHz, CDCl$_3$) δ 162.8, 139.2, 138.4, 129.3, 128.7, 128.4, 127.8, 124.2, 71.4, 31.3, 28.9, 28.7, 25.2, 22.4, 13.9. HRMS (ESI, TOF MS) m/z calculated for $C_{23}H_{28}N_7O$ [M + H]$^+$: 418.2355, found: 418.2353. | 60% (c) |

| # | Name | Characterization | Yield |
|---|---|---|---|
| 42 | 2-(4-(3-chloropropyl)-1H-1,2,3-triazol-1-yl)-2,2-diphenyl-1-(1H-tetrazol-5-yl)ethan-1-ol | Mp: 114-116° C. $^1$H NMR (300 MHz, CDCl$_3$) δ 7.25-7.39 (m, 12H), 7.02 (bs, 1H), 6.83 (b, 4H), 3.55 (m, 2H), 2.82 (m, 2H), 2.11 (m, 2H). $^{13}$C NMR (75 MHz, CDCl$_3$) δ 139.1, 138.3, 129.5, 128.8, 128.5, 127.8, 125.2, 71.2, 43.9, 31.4, 22.4. HRMS (ESI, TOF MS) m/z calculated for C$_{20}$H$_{21}$N$_7$OCl [M + H]$^+$: 410.1496, found: 410.1490. | 78% (c) |
| 43 | tert-butyl 1-(2-hydroxy-1,1-diphenyl-2-(1H-tetrazol-5-yl)ethyl)-1H-1,2,3-triazole-4-carboxylate | Mp: 122-124° C. $^1$H NMR (300 MHz, CDCl$_3$) δ 7.69 (s, 1H), 7.43 (b, 5H), 7.27 (b, 3H), 6.94-6.97 (m, 3H), 1.59 (s, 9H). $^{13}$C NMR (75 MHz, CDCl$_3$) δ 159.2, 155.5, 139.7, 138.1, 130.0, 129.5, 128.9, 128.8, 128.5, 127.6, 83.1, 70.7, 27.9. HRMS (ESI, TOF MS) m/z calculated for C$_{22}$H$_{23}$N$_7$ONa [M + Na]$^+$: 456.1760, found: 456.1754. | 49% (c) |

These results evidence that the applicant successfully conceived and reduced to practice a CuAAC reaction between the alpha-hydroxy-beta-azido-tetrazoles and terminal alkynes.

Procedures (c) and (d) are thus efficient methods to prepare a wide range of alpha-hydroxy-beta-triazolo-tetrazoles compounds.

Example 7: Triazole Alkynes

Hereafter are provided triazoles alkynes according to the invention. R$^1$, R$^2$ and R$^3$ groups refer to formula (IV):

(IV)

| # | R$^1$ | R$^2$ | R$^3$ | Formula | Name |
|---|---|---|---|---|---|
| 44 | pentyl (cyclohexyl) | | Ph | | 1-(1-ethynyl-cyclohexyl)-4-phenyl-1H-1,2,3-triazole |
| 45 | hexyl (cycloheptyl) | | Ph | | 1-(1-ethynyl-cycloheptyl)-4-phenyl-1H-1,2,3-triazole |
| 46 | heptyl (cyclooctyl) | | Ph | | 1-(1-ethynyl-cyclooctyl)-4-phenyl-1H-1,2,3-triazole |
| 47 | heptyl (cyclooctyl) | | tBuAc | | tert-butyl 1-(1-ethynyl-cyclooctyl)-1H-1,2,3-triazole-4-carboxylate |

-continued

| # | R¹ | R² | R³ | Formula | Name |
|---|---|---|---|---|---|
| 48 | heptyl (cyclo-octyl) | 3-chloropropyl | Cl | | 4-(3-chloropropyl)-1-(1-ethynyl-cyclooctyl)-1H-1,2,3-triazole |
| 49 | heptyl (cyclo-octyl) | 2-hydroxy-ethyl | OH | | 2-(1-(1-ethynyl-cyclooctyl)-1H-1,2,3-triazol-4-yl)ethan-1-ol |
| 50 | Et | Et | Ph | | 1-(3-ethylpent-1-yn-3-yl)-4-phenyl-1H-1,2,3-triazole |
| 51 | Ph | H | hexyl | | 4-hexyl-1-(1-phenylprop-2-yn-1-yl)-1H-1,2,3-triazole |
| 52 | Ph | Ph | hexyl | 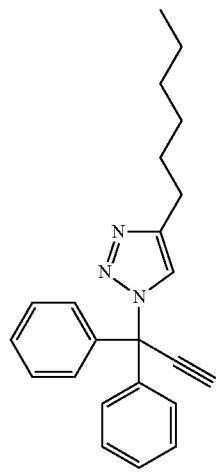 | 1-(1,1-diphenylprop-2-yn-1-yl)-4-hexyl-1H-1,2,3-triazole |

These compounds may be prepared as disclosed in Example 8.

Example 8: Synthesis of Triazole Alkenes

Materials and Methods

Procedures for the Reaction of α-Hydroxy-β-Triazole-Tetrazoles with Carbodiimides:

Procedure (e), with Diisopropylcarbodiimide (DIC):

The alpha-hydroxy-beta-triazole-tetrazole (0.35 mmol) was dissolved in dichloromethane (10 mL). DIC (0.42 mmol) was added. The mixture was stirred at room temperature for 18 hours, and then concentrated under reduced pressure. The residue was purified by flash chromatography on silica gel.

Procedure (f), with N-(3-Dimethylaminopropyl)-N'-Ethylcarbodiimide (EDC):

The alpha-hydroxy-beta-triazole-tetrazole (0.1 mmol) was dissolved in dichloromethane (5 mL). EDC (0.12 mmol) was added and the mixture was stirred at room temperature for 18 hours. The mixture was diluted with dichloromethane and the resulting solution was washed successively with solutions of aqueous 0.5M HCl, aqueous saturated NaCl and aqueous saturated NaHCO₃. The organic layer was dried over MgSO₄ and concentrated under reduced pressure. The residue was purified by flash chromatography on silica gel.

Results

Hereafter are provided the yield and physical characterization of triazole alkynes according to the invention, prepared by the above procedures.

Compounds #44-52 were prepared from the corresponding alpha-hydroxy-beta-triazolo-tetrazoles disclosed in Example 5 and 6.

| # | Name | Characterization | Yield |
|---|------|------------------|-------|
| 44 | 1-(1-ethynylcyclohexyl)-4-phenyl-1H-1,2,3-triazole | Mp: 114-116° C. $^1$H NMR (300 MHz, CDCl$_3$) δ 8.18 (d, J = 4.6 Hz, 1H), 7.85-7.89 (m, 2H), 7.26-7.47 (m, 3H), 2.78 (d, J = 4.7 Hz, 1H), 2.25-2.43 (m, 4H), 1.77-1.88 (m, 5H), 1.28-1.43 (m, 1H). $^{13}$C NMR (75 MHz, CDCl$_3$) δ 146.7, 130.7, 128.7, 128.0, 125.7, 118.5, 82.4, 76.2, 61.5, 38.6, 24.7, 23.1. HRMS (ESI, TOF MS) m/z calculated for C$_{16}$H$_{18}$N$_3$ [M + H]$^+$ 252.1501, found: 252.1498. | 69% (e) |
| 45 | 1-(1-ethynylcycloheptyl)-4-phenyl-1H-1,2,3-triazole | Mp: 80-81° C. $^1$H NMR (300 MHz, CDCl$_3$) δ 8.18 (s, 1H), 7.85 (m, 2H), 7.40-7.45 (m, 2H), 7.33 (m, 1H), 2.79 (s, 1H), 2.59-2.63 (m, 2H), 2.27-2.34 (m, 2H), 1.66-1.87 (m, 8H). $^{13}$C NMR (75 MHz, CDCl$_3$) δ 146.5, 130.6, 128.7, 128.0, 125.7, 118.5, 83.7, 75.4, 64.6, 42.1, 27.9, 22.7. HRMS (ESI, TOF MS) m/z calculated for C$_{17}$H$_{20}$N$_3$ [M + H]$^+$ 266.1657, found: 266.1655. | 61% (c) |
| 46 | 1-(1-ethynylcyclooctyl)-4-phenyl-1H-1,2,3-triazole | Mp: 78° C. $^1$H NMR (300 MHz, CDCl$_3$) δ 8.15 (s, 1H), 7.85 (m, 2H), 7.40-7.45 (m, 2H), 7.33 (t, J = 7.2 Hz, 1H), 2.72 (s, 1H), 2.64-2.71 (m, 2H), 2.24-2.33 (m, 2H), 1.63-1.81 (m, 12H). $^{13}$C NMR (75 MHz, CDCl$_3$) δ 146.7, 130.6, 128.7, 128.0, 125.7, 118.5, 83.9, 74.7, 64.3, 37.0, 27.7, 24.4, 22.4. HRMS (ESI, TOF MS) m/z calculated for C$_{18}$H$_{22}$N$_3$ [M + H]$^+$: 280.1814, found: 280.1817 | 73% (e) |
| 47 | tert-butyl 1-(1-ethynylcyclooctyl)-1H-1,2,3-triazole-4-carboxylate | $^1$H NMR (300 MHz, CDCl$_3$) δ 8.35 (s, 1H), 2.73 (s, 1H), 2.57-2.62 (m, 2H), 2.18-2.24 (m, 2H), 1.61-1.75 (m, 21H). $^{13}$C NMR (75 MHz, CDCl$_3$) δ 160.2, 140.5, 130.6, 125.9, 83.1, 82.2, 75.2, 64.8, 37.0, 28.2, 27.6, 24.3, 22.3. HRMS (ESI, TOF MS) m/z calculated for C$_{17}$H$_{26}$N$_3$O$_2$ [M + H]$^+$ 304.2025, found: 304.2031. | 76% (f) |
| 48 | 4-(3-chloropropyl)-1-(1-ethynylcyclooctyl)-1H-1,2,3-triazole | $^1$H NMR (300 MHz, CDCl$_3$) δ 7.69 (s, 1H), 3.59 (t, J = 6.4 Hz, 2H), 2.89 (t, J = 7.7 Hz, 2H), 2.67 (s, 1H), 2.57-2.64 (m, 2H), 2.16-2.26 (m, 4H), 1.62-1.76 (m, 10H). $^{13}$C NMR (75 MHz, CDCl$_3$) δ 145.6, 119.9, 83.9, 74.4, 63.9, 44.3, 36.9, 31.9, 27.7, 24.3, 22.7, 22.4. HRMS (ESI, TOF MS) m/z calculated for C$_{15}$H$_{23}$N$_3$Cl [M + H]$^+$ 280.1581, found: 280.1587. | 75% (f) |
| 49 | 2-(1-(1-ethynylcyclooctyl)-1H-1,2,3-triazol-4-yl)ethan-1-ol | $^1$H NMR (300 MHz, CDCl$_3$) δ 7.76 (s, 1H), 3.95 (t, J = 5.6 Hz, 1H), 2.86-2.98 (m, 3H), 2.67 (s, 1H), 2.55-2.64 (m, 2H), 2.17-2.25 (m, 2H), 1.61-1.76 (m, 10H). $^{13}$C NMR (75 MHz, CDCl$_3$) δ 144.5, 120.3, 83.8, 74.5, 64.0, 61.5, 36.9, 28.6, 27.7, 24.3, 22.4. HRMS (ESI, TOF MS) m/z calculated for C$_{14}$H$_{22}$N$_3$O [M + H]$^+$: 248.1763, found: 248.1770. | 46% (f) |
| 50 | 1-(3-ethylpent-1-yn-3-yl)-4-phenyl-1H-1,2,3-triazole | Mp: 36-38° C. $^1$H NMR (300 MHz, CDCl$_3$) δ 8.17 (s, 1H), 7.87-7.90 (m, 2H), 7.40-7.45 (m, 2H), 7.33 (m, 1H), 2.79 (s, 1H), 2.38-2.50 (m, 2H), 2.07-2.19 (m, 2H), 0.89 (t, J = 7.4 Hz 6H). $^{13}$C NMR (75 MHz, CDCl$_3$) δ 146.0, 130.7, 128.7, 127.9, 125.6, 120.6, 81.2, 76.3, 66.0, 34.8, 8.5. HRMS (ESI, TOF MS) m/z calculated for C$_{15}$H$_{18}$N$_3$ [M + H]$^+$: 240.1501, found: 240.1502 | 73% (e) |
| 51 | 4-hexyl-1-(1-phenylprop-2-yn-1-yl)-1H-1,2,3-triazole | Mp: 59-61° C. $^1$H NMR (300 MHz, CDCl$_3$) δ 7.37-7.48 (m, 6H), 6.67 (d, J = 2.0 Hz, 1H), 2.82 (d, J = 2.4 Hz, 1H), 2.68 (t, J = 7.5 Hz, 2H), 1.59-1.69 (m, 2H), 1.28-1.36 (m, 6H), 0.86 (t, J = 7.0 Hz, 3H). $^{13}$C NMR (75 MHz, CDCl$_3$) δ 149.0, 135.6, 129.2, 128.9, 127.0, 119.0, 78.1, 55.5, 31.4, 29.2, 28.8, 25.7, 22.5, 13.9. HRMS (ESI, TOF MS) m/z calculated for C$_{17}$H$_{22}$N$_3$ [M + H]$^+$: 268.1814, found: 268.1812. | 75% (e) |
| 52 | 1-(1,1-diphenylprop-2-yn-1-yl)-4-hexyl-1H-1,2,3-triazole | Mp: 59-61° C. $^1$H NMR (300 MHz, CDCl$_3$) δ 7.25-7.44 (m, 11H), 3.09 (s, 1H), 2.74 (t, J = 8.0 Hz, 1H), 1.63-1.70 (m, 2H), 1.29-1.33 (m, 6H), 0.80 (b, 3H). $^{13}$C NMR (75 MHz, CDCl$_3$) δ 147.7, 140.3, 128.8, 128.4, 127.9, 121.6, 83.2, 77.6, 69.1, 31.5, 29.3, 28.9, 25.7, 22.5, 14.0. HRMS (ESI, TOF MS) m/z calculated for C$_{23}$H$_{26}$N$_3$ [M + H]$^+$: 344.2127, found: 344.2132. | 62% (f) |

Surprisingly, the formation of a 5-membered cycle or heterocycle was never observed by the applicant when carrying out the reaction of alpha-hydroxy-beta-triazolo-tetrazoles with carbodiimides. The triazoles alkyne is thus the only product of the reaction.

These results evidence that the alpha-hydroxy-beta-triazolo-tetrazoles according to the invention may be efficiency converted to triazoles alkynes, by the very broad procedures (e) and (f) according to the invention.

Example 9: Di-Triazoles and Synthesis Thereof

Compounds

Hereafter are provided di-triazoles according to the invention. $R^1$, $R^2$, $R^3$ and $R^4$ groups refer to formula (V):

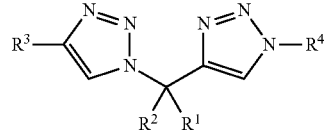

(V)

| # | $R^1$ | $R^2$ | $R^3$ | $R^4$ | Formula | Name |
|---|---|---|---|---|---|---|
| 53 | pentyl | Ph (cyclohexyl) | | octyl | | 1-octyl-4-(1-(4-phenyl-1H-1,2,3-triazol-1-yl)cyclohexyl)-1H-1,2,3-triazole |
| 54 | pentyl | Ph (cyclohexyl) | | bis (cyclopentadienyl) iron | | 1-[bis(η5-cyclopentadienyl) iron]-4-(1-(4-phenyl-1H-1,2,3-triazol-1-yl)cyclohexyl)-1H-1,2,3-triazole |
| 55 | pentyl | Ph (cyclohexyl) | | carbohydrate | | (2S,3S,4R,5S,6S)-2-(acetoxymethyl)-6-(4-(1-(4-phenyl-1H-1,2,3-triazol-1-yl)cyclohexyl)-1H-1,2,3-triazol-1-yl)tetrahydro-2H-pyran-3,4,5-triyl triacetate |

-continued

| # | R¹ | R² | R³ | R⁴ | Formula | Name |
|---|---|---|---|---|---|---|
| 56 | pentyl (cyclohexyl) | Ph | | —CH₂CH(COOMe)NHBoc | | methyl 2-((tert-butoxycarbonyl)amino)-3-(4-(1-(4-phenyl-1H-1,2,3-triazol-1-yl)cyclohexyl)-1H-1,2,3-triazol-1-yl)propanoate |
| 57 | heptyl (cyclooctyl) | Ph | | octyl | | 1-octyl-4-(1-(4-phenyl-1H-1,2,3-triazol-1-yl)cyclooctyl)-1H-1,2,3-triazole |
| 58 | heptyl (cyclooctyl) | Ph | | EtCOO-propyl | | ethyl 4-(4-(1-(4-phenyl-1H-1,2,3-triazol-1-yl)cyclooctyl)-1H-1,2,3-triazol-1-yl)butanoate |

-continued

| # | R¹ | R² | R³ | R⁴ | Formula | Name |
|---|---|---|---|---|---|---|
| 59 | heptyl (cyclooctyl) | Ph | | pyren-1-ylmethyl | | 4-phenyl-1-(1-(1-(pyren-1-ylmethyl)-1H-1,2,3-triazol-4-yl)cyclooctyl)-1H-1,2,3-triazole |
| 60 | heptyl (cyclooctyl) | Ph | | benzyl | | 1-benzyl-4-(1-(4-phenyl-1H-1,2,3-triazol-1-yl)cyclooctyl)-1H-1,2,3-triazole |
| 61 | heptyl (cyclooctyl) | Ph | | —C(Et)₂—CH(OH)-Tz | | 2-ethyl-2-(4-(1-(4-phenyl-1H-1,2,3-triazol-1-yl)cyclooctyl)-1H-1,2,3-triazol-1-yl)-1-(1H-tetrazol-5-yl)butan-1-ol |

Materials and Methods

Procedure (g) for the CuAAC Reaction of Triazole Alkynes:

The triazole alkyne substrate (0.1 mmol) was dissolved in n-BuOH (1 mL). An azide (0.3 mmol) was added. A solution of sodium ascorbate (0.02 mmol in 0.25 mL water) was added, followed by a solution of copper sulphate (0.01 mmol in 0.25 mL water). The mixture was stirred at room temperature for 48 hours. The organic phase was separated and concentrated under reduced pressure. The residue was purified by flash chromatography on silica gel.

Results

Hereafter are provided the yield and physical characterization of di-triazoles according to the invention, prepared by the above procedure (g).

Compounds #53-61 were prepared from the corresponding triazole alkynes disclosed in Examples 7 and 8 and from the appropriate $R^4$—$N_3$ azide.

| # | Name | Characterization | Yield |
|---|------|------------------|-------|
| 53 | 1-octyl-4-(1-(4-phenyl-1H-1,2,3-triazol-1-yl)cyclohexyl)-1H-1,2,3-triazole | Mp: 110-112° C. $^1$H NMR δ 7.93 (s, 1H), 7.81-7.84 (m, 2H), 7.26-7.42 (m, 4H), 4.26 (t, J = 6.9 Hz, 2H), 2.65-2.80 (m, 4H), 1.84 (b, 2H), 1.57-1.64 (m, 6H), 1.23-1.27 (m, 10H), 0.85 (t, J = 6.1 Hz, 3H). $^{13}$C NMR (75 MHz, CDCl$_3$) δ 150.8, 147.2, 130.5, 128.7, 128.0, 125.6, 121.1, 118.3, 62.3, 50.5, 35.7, 31.6, 30.1, 28.9, 28.8, 26.4, 24.8, 22.5, 22.0, 14.0. HRMS (ESI, TOF MS) m/z calculated for C$_{24}$H$_{35}$N$_6$ [M + H]$^+$: 407.2923, found: 407.2924. | 98% |
| 54 | 1-[bis(η5-cyclopentadienyl)iron]-4-(1-(4-phenyl-1H-1,2,3-triazol-1-yl)cyclohexyl)-1H-1,2,3-triazole | Mp: 157-163° C. (dec.). $^1$H NMR δ 7.92 (s, 1H), 7.80-7.83 (m, 2H), 7.27-7.40 (m, 4H), 5.22 (bs, 2H), 4.14-4.24 (m, 9H), 2.65-2.75 (m, 4H), 1.84 (b, 2H), 1.58-1.62 (m, 6H). $^{13}$C NMR (75 MHz, CDCl$_3$) δ 150.8, 147.3, 130.6, 128.7, 127.9, 125.5, 120.6, 118.3, 80.4, 69.1, 68.8, 62.1, 50.1, 35.7, 24.8, 21.9. HRMS (ESI TOF MS) m/z calculated for C$_{27}$H$_{28}$N$_6$Fe [M + H]$^+$: 492.1724, found: 492.1729. | 75% |
| 55 | 2-(acetoxymethyl)-6-(4-(1-(4-phenyl-1H-1,2,3-triazol-1-yl)cyclohexyl)-1H-1,2,3-triazol-1-yl)tetrahydro-2H-pyran-3,4,5-triyl triacetate | $^1$H NMR δ 7.86-7.84 (m, 3H), 7.66 (s, 1H), 7.30-7.42 (m, 3H), 5.82 (d, J = 9.0 Hz, 1H), 5.23-5.39 (m, 2H), 5.33 (m, 1H), 4.27-4.33 (m, 1H), 4.11-4.15 (m, 1H), 3.99-4.02 (m, 1H), 2.70-2.81 (m, 4H), 2.07 (s, 3H), 2.05 (s, 3H), 2.01 (s, 3H), 1.84 (s, 3H), 1.57-1.62 (m, 6H). $^{13}$C NMR (75 MHz, CDCl$_3$) δ 170.4, 169.8, 169.2, 168.8, 130.6, 128.7, 128.0, 125.5, 120.5, 85.9, 75.2, 72.2, 70.6, 67.6, 62.3, 61.4, 36.0, 35.6, 24.8, 22.0, 21.9, 20.6, 20.4, 20.0. HRMS (ESI, TOF MS) m/z calculated for C$_{30}$H$_{37}$N$_6$O$_9$ [M + H]$^+$: 625.2622, found: 625.2626. | 93% |
| 56 | methyl 2-((tert-butoxycarbonyl)amino)-3-(4-(1-(4-phenyl-1H-1,2,3-triazol-1-yl)cyclohexyl)-1H-1,2,3-triazol-1-yl)propanoate | $^1$H NMR δ 7.81-7.89 (m, 3H), 7.29-7.41 (m, 4H), 5.42 (d, J = 6.9 Hz), 4.66-4.76 (m, 3H), 3.72 (s, 3H), 2.61-2.77 (m, 4H), 1.55-1.62 (m, 6H), 1.38 (s, 9H). $^{13}$C NMR (75 MHz, CDCl$_3$) δ 169.3, 154.9, 130.4, 128.7, 128.0, 125.6, 122.8, 118.4, 80.7, 62.2, 53.6, 53.0, 51.0, 35.8, 35.7, 28.1, 24.8, 22.0. HRMS (ESI, TOF MS) m/z calculated for C$_{25}$H$_{34}$N$_7$O$_4$ [M + H]$^+$: 496.2672, found: 496.2669. | 89% |
| 57 | 1-octyl-4-(1-(4-phenyl-1H-1,2,3-triazol-1-yl)cyclooctyl)-1,2,3-triazole | $^1$H NMR δ 7.93 (s, 1H), 7.80-7.83 (m, 2H), 7.27-7.41 (m, 4H), 4.29 (t, J = 6.9 Hz, 2H), 2.75-2.96 (m, 4H), 1.84-1.89 (m, 2H), 1.65 (b, 10H), 1.24-1.28 (m, 10H), 0.86 (t, 1H- J = 6.1 Hz, 3H). $^{13}$C NMR (75 MHz, CDCl$_3$) δ 151.2, 130.7, 128.7, 127.9, 125.5, 121.3, 118.6, 66.1, 50.4, 33.5, 31.6, 30.0, 28.9, 28.8, 27.9, 26.4, 24.6, 22.5, 22.0, 14.0. HRMS (ESI, TOF MS) m/z calculated for C$_{26}$H$_{38}$N$_6$Na [M + Na]$^+$ 457.3056, found: 457.3061. | 92% |
| 58 | ethyl 4-(4-(1-(4-phenyl-1H-1,2,3-triazol-1-yl)cyclooctyl)-1H-1,2,3-triazol-1-yl)butanoate | $^1$H NMR δ 7.95 (s, 1H), 7.80-7.83 (m, 2H), 7.27-7.46 (m, 4H), 4.38 (t, J = 6.7 Hz, 2H), 4.10 (m, 2H), 2.73-2.96 (m, 4H), 2.15-2.35 (m, 4H), 1.64 (b, 10H), 1.23 (m, J = 6.5 Hz, 3H). $^{13}$C NMR (75 MHz, CDCl$_3$) δ 172.1, 151.2, 146.9, 130.6, 128.7, 127.9, 125.5, 121.7, 118.7, 66.1, 60.7, 49.4, 33.5, 30.7, 27.9, 25.2, 24.6, 21.9, 14.1. HRMS (ESI, TOF MS) m/z calculated for C$_{24}$H$_{32}$N$_6$O$_2$Na [M + Na]$^+$: 459.2484, found: 459.2479. | 83% |
| 59 | 4-phenyl-1-(1-(1-(pyren-1-ylmethyl)-1H-1,2,3-triazol-4-yl)cyclooctyl)-1H-1,2,3-triazole | $^1$H NMR δ 8.02-8.25 (m, 8H), 7.73-7.94 (m, 4H), 7.27-7.36 (m, 4H), 6.20 (bs, 2H), 2.62-2.85 (m, 4H), 1.55 (b, 10H). $^{13}$C NMR (75 MHz, CDCl$_3$) δ 151.3, 132.2, 131.1, 130.5, 129.0, 128.7, 128.3, 128.0, 127.7, 127.2, 126.4, 126.3, 125.9, 125.8, 125.6, 125.0, 124.9, 124.4, 121.7, 121.6, 118.7, 66.3, 52.6, 33.3, 27.8, 24.6, 21.9. HRMS (ESI, TOF MS) m/z calculated for C$_{35}$H$_{32}$N$_6$Na [M + Na]$^+$: 559.2586, found: 559.2584. | 100% |
| 60 | 1-benzyl-4-(1-(4-phenyl-1H-1,2,3-triazol-1-yl)cyclooctyl)-1H-1,2,3-triazole | Mp: 133-134° C. $^1$H NMR δ 7.97 (s, 1H), 7.82-7.85 (m, 2H), 7.27-7.41 (m, 9H), 5.50 (bs, 2H), 2.73-2.95 (m, 4H), 1.65 (b, 10H). $^{13}$C NMR (75 MHz, CDCl$_3$) δ 151.5, 146.9, 134.1, 130.5, 129.1, 128.7; 128.0, 127.9, 125.5, 121.5, 118.6, 66.1, 54.2, 33.4, 27.9, 24.6, 21.9. HRMS (ESI, TOF MS) m/z calculated for C$_{25}$H$_{29}$N$_6$ [M + H]$^+$: 413.2454, found: 413.2464 | 90% |
| 61 | 2-ethyl-2-(4-(1-(4-phenyl-1H-1,2,3-triazol-1-yl)cyclooctyl)-1H-1,2,3-triazol-1-yl)-1-(1H-tetrazol-5-yl)butan-1-ol | $^1$H NMR δ 8.59 (s, 1H), 8.33, (s, 1H), 8.18-8.21 (m, 2H), 7.32-7.44 (m, 3H), 2.54-3.05 (m, 8H), 1.41-1.59 (b, 10H), 0.94-1.03 (m, 6H). $^{13}$C NMR (75 MHz, pyridine-d$_5$) δ 151.2, 130.7, 128.7, 127.9, 125.5, 121.3, 118.6, 66.1, 50.4, 33.5, 31.6, 30.0, 28.9, 28.8, 27.9, 26.4, 24.6, 22.5, 22.0, 14.0. HRMS (ESI, TOF MS) m/z calculated for C$_{25}$H$_{35}$N$_{10}$O [M + H]$^+$: 491.2995, found: 491.2996. | 91% |

These results evidence that the triazoles alkynes according to the invention may be efficiency reacted with azides in CuAAC conditions to prepare various di-triazoles compounds.

Example 10: Poly-Triazoles and Synthesis Thereof

Compounds

Hereafter are provided poly-triazoles according to the invention.

| # | Formula | Name |
|---|---------|------|
| 62 | | 1-(3-ethylpent-1-yn-3-yl)-4-(1-(4-phenyl-1H-1,2,3-triazol-1-yl)cyclooctyl)-1H-1,2,3-triazole |
| 63 | | 1-(1-ethynylcyclooctyl)-4-(3-(4-(1-(4-phenyl-1H-1,2,3-triazol-1-yl)cyclooctyl)-1H-1,2,3-triazol-1-yl)pentan-3-yl)-1H-1,2,3-triazole |
| 64 | | 1-benzyl-4-(1-(4-(3-(4-(1-(4-phenyl-1H-1,2,3-triazol-1-yl)cyclooctyl)-1H-1,2,3-triazol-1-yl)pentan-3-yl)-1H-1,2,3-triazol-1-yl)cyclooctyl)-1H-1,2,3-triazole |

Materials and Methods

Procedure for Synthesis of Bis-Triazole Alkyne #62:

2-Azido-2-ethyl-1-(1H-tetrazol-5-yl)-butan-1-ol (28 mg, 0.18 mmol) #26 and 1-(1-ethynyl-cyclooctyl)-4-phenyl-1H-[1,2,3]triazole (45 mg, 0.16 mmol) #46 were dissolved in nBuOH (2 mL). TBTA (tris((1-benzyl-1H-1,2,3-triazolyl)methyl)amine) (10.5 mg, 0.02 mmol) was added. A solution of sodium ascorbate (11 mg, 0.05 mmol in 0.5 mL water) was added, followed by a solution of copper sulphate (5 mg, 0.02 mmol in 0.5 mL water). The mixture was stirred at room temperature for 48 hours. The mixture was concentrated under reduced pressure.

The residue was dissolved in 1,2-dichloroethane (3 mL). DIC (0.035 mL, 0.22 mmol) was added. The mixture was stirred at 50° C. for 3 hours, and then concentrated under reduced pressure. The residue was purified by flash chromatography on silica gel using petroleum ether/EtOAc: 90/10 as eluent (Rf=0.18). The bis-triazole alkyne was isolated as a white solid (41 mg, 62% yield).

Procedure for Synthesis of Tris-Triazole Alkyne #63:

(1-Azido-cyclooctyl)-(1H-tetrazol-5-yl)-methanol (30 mg, 0.12 mmol) #30 and the bis-triazole alkyne #62 (41 mg, 0.1 mmol) were dissolved in n-BuOH (2 mL) and THF (1 mL). TBTA (tris((1-benzyl-1H-1,2,3-triazolyl)methyl)amine) (8 mg, 0.015 mmol) was added. A solution of sodium ascorbate (7 mg, 0.035 mmol in 0.5 mL water) was added, followed by a solution of copper sulphate (3 mg, 0.012 mmol in 0.5 mL water). The mixture was stirred at room temperature for 5 days. The mixture was concentrated under reduced pressure.

The residue was dissolved in 1,2-dichloroethane (2 mL). DIC (0.02 mL, 0.14 mmol) was added. The mixture was stirred at room temperature for 4 hours, and then concentrated under reduced pressure. The residue was purified by flash chromatography on silica gel using petroleum ether/EtOAc: 75/25 as eluent (Rf=0.27). The tris-triazole alkyne was isolated as a white solid (31 mg, 52% yield).

Procedure for Synthesis of Tetra-Triazole #64:

The tris-triazole alkyne #63 (19 mg, 0.032 mmol) was dissolved in n-BuOH (1 mL). Benzyl azide (0.01 mL, 0.085 mmol) was added. A solution of sodium ascorbate (3 mg, 0.015 mmol in 0.25 mL water) was added, followed by a solution of copper sulphate (1.2 mg, 0.005 mmol in 0.25 mL water). The mixture was stirred at room temperature for 24 hours. The mixture was concentrated under reduced pressure. The residue was purified by flash chromatography on silica gel using dichloromethane/MeOH: 98/2 as eluent (Rf=0.34). The tetra-triazole was isolated as white foam (20 mg, 86% yield).

Results

Hereafter are provided the yield and physical characterization of poly-triazoles according to the invention, prepared by the above procedures.

| # | Name | Characterization | Yield |
|---|---|---|---|
| 62 | 1-(3-ethylpent-1-yn-3-yl)-4-(1-(4-phenyl-1H-1,2,3-triazol-1-yl)cyclooctyl)-1H-1,2,3-triazole | $^1$H NMR (300 MHz, CDCl$_3$) δ 7.90 (s, 1H), 7.80-7.83 (m, 3H), 7.27-7.42 (m, 3H), 2.92-3.00 (m, 2H), 2.73-2.80 (m, 2H), 2.72 (s, 1H), 2.28-2.40 (m, 2H), 2.03-2.14 (m, 2H), 1.66 (b, 10H), 0.81 (m, 6H). $^{13}$C NMR (75 MHz, CDCl$_3$) δ 149.3, 146.9, 130.7, 128.7, 127.9, 125.5, 122.6, 118.5, 80.7, 76.7, 66.2, 66.1, 34.7, 33.5, 27.9, 24.7, 22.0, 8.5. HRMS (ESI, TOF MS) m/z calculated for C$_{25}$H$_{32}$N$_6$Na [M + Na]$^+$: 439.2586, found: 439.2585. | 62% |
| 63 | 1-(1-ethynylcyclooctyl)-4-(3-(4-(1-(4-phenyl-1H-1,2,3-triazol-1-yl)cyclooctyl)-1H-1,2,3-triazol-1-yl)pentan-3-yl)-1H-1,2,3-triazole | $^1$H NMR (300 MHz, CDCl$_3$) δ 7.91 (s, 1H), 7.79-7.82 (m, 3H), 7.57 (s, 1H), 7.27-7.42 (m, 3H), 2.89-2.97 (m, 2H), 2.71-2.77 (m, 2H), 2.65 (s, 1H), 2.44-2.58 (m, 6H), 2.15-2.22 (m, 2H), 1.61-1.74 (m, 20H), 0.76 (m, 6H). $^{13}$C NMR (75 MHz, CDCl$_3$) δ 150.2, 147.9, 146.9, 130.6, 128.7, 127.9, 125.6, 121.0, 121.0, 118.7, 83.4, 75.0, 67.0, 66.2, 64.4, 37.0, 33.5, 30.3, 27.9, 27.6, 24.7, 24.3, 22.4, 22.0, 7.8. HRMS (ESI, TOF MS) m/z calculated for C$_{35}$H$_{47}$N$_9$Na [M + Na]$^+$: 616.3852, found: 616.3859. | 52% |
| 64 | 1-benzyl-4-(1-(4-(3-(4-(1-(4-phenyl-1H-1,2,3-triazol-1-yl)cyclooctyl)-1H-1,2,3-triazol-1-yl)pentan-3-yl)-1H-1,2,3-triazol-1-yl)cyclooctyl)-1H-1,2,3-triazole | $^1$H NMR (300 MHz, CDCl$_3$) δ 7.91 (s, 1H), 7.80-7.82 (m, 2H), 7.57 (s, 1H), 7.51 (s, 1H), 7.21-7.41 (m, 9H), 5.47 (s, 2H), 2.60-2.92 (m, 8H), 2.38-2.51 (m, 4H), 1.52-1.60 (m, 20H), 0.68-0.72 (m, 6H). $^{13}$C NMR (75 MHz, CDCl$_3$) δ 151.1, 148.1, 142.4, 142.2, 134.2, 130.5, 129.1, 128.8, 128.7, 128.0, 125.6, 121.5, 121.3, 121.2, 118.9, 118.7, 67.0, 66.4, 54.2, 33.6, 33.5, 30.3, 27.9, 27.8, 24.7, 24.6, 22.0, 21.9, 7.8. HRMS (ESI, TOF MS) m/z calculated for C$_{42}$H$_{55}$N$_{12}$ [M + H]$^+$: 727.4673, found: 727.4678. | 86% |

These results evidence that successive iterations of the reactions according to the invention may be used to efficiently prepare poly-triazoles compounds substituted by different alkyl and aryl groups.

The invention claimed is:

1. An alpha-hydroxy-beta-azido-tetrazole compound of formula (I):

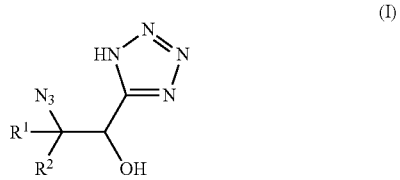

(I)

wherein R$^1$ and R$^2$ are each independently selected from the groups consisting of hydrogen, hydrocarbyl, aryl, heteroaryl, hydrocarbylaryl, arylhydrocarbyl, hydrocarbylheteroaryl, and heteroarylhydrocarbyl groups;

or R$^1$ and R$^2$ form together a hydrocarbyl, aryl, heteroaryl, hydrocarbylaryl, arylhydrocarbyl, hydrocarbylheteroaryl or heteroarylhydrocarbyl group;

wherein the group is optionally substituted by at least one hydrocarbyl, aryl, heteroaryl, oxo, hydroxyl, amido, amino, nitro, carboxylo, formyl, halo, thioxo or sulfhydryl; and wherein the group is optionally interrupted or terminated by at least one of —O—, —S—, or —NR$^N$—, wherein R$^N$ is selected from the group consisting of hydrogen, hydrocarbyl, aryl, and a combination thereof, and wherein the nitrogen and/or sulfur atoms are optionally oxidized;

or a stereoisomer, salt or solvent thereof.

2. The compound according to claim 1, wherein R$^1$ and R$^2$ are each independently selected from the group consisting of hydrogen, alkyl, alkenyl, aryl, heteroaryl, alkylaryl, arylalkyl, alkenylaryl, and arylalkenyl groups;

wherein the groups are optionally substituted by at least one hydroxyl, alkyl, alkenyl, aryl, alkylaryl, arylalkyl, amino, nitro, halo and sulfhydryl; and wherein the groups are optionally interrupted or terminated by at least one of —O—, —S—, or —NR$^N$—, wherein R$^N$ is selected from the group consisting of hydrogen, alkyl, alkenyl, and a combination thereof.

3. The compound according to claim 1, wherein R$^1$ and R$^2$ are each independently selected from the group consisting of hydrogen, alkyl, alkenyl, aryl, heteroaryl, alkylaryl and alkenylaryl groups;

wherein the groups are optionally substituted by at least one hydroxyl, alkyl, amino, nitro, halo or sulfhydryl; and wherein the groups are optionally interrupted or terminated by at least one of —O—, —S—, or —NR$^N$—, wherein R$^N$ is selected from the group consisting of hydrogen, alkyl, alkenyl, aryl, alkylaryl, and arylalkyl.

4. The compound according to claim 1, wherein R$^1$ and R$^2$ are each independently selected from the group consisting of hydrogen, alkyl, aryl and alkenylaryl groups; and the groups are optionally substituted by at least one halo group.

5. The compound according to claim 1, wherein R$^1$ and R$^2$ form together an alkyl, alkenyl, aryl, alkylaryl, arylalkyl, alkenylaryl or arylalkenyl group;

wherein the group is optionally substituted by at least one hydroxyl, alkyl, alkenyl, aryl, alkylaryl, arylalkyl, amino, nitro, halo or sulfhydryl; and wherein the group is optionally interrupted or terminated by at least one of —O—, —S—, or —NR$^N$—, wherein R$^N$ is selected from the group consisting of hydrogen, alkyl, alkenyl, aryl, and a combination thereof.

6. The compound according to claim 1, wherein R$^1$ and R$^2$ form together an alkyl, alkylaryl or arylalkyl group;

wherein the group is optionally substituted by at least one hydroxyl, alkyl, amino, nitro or halo; and wherein the group is optionally interrupted or terminated by at least one of —O— or —NR$^N$—, wherein R$^N$ is selected from the group consisting of hydrogen, alkyl, alkenyl, aryl, alkylaryl, and arylalkyl.

7. The compound according to claim 1, wherein $R^1$ and $R^2$ form together an alkyl or aryl group.

8. The compound according to claim 1, selected from the group consisting of: 2-azido-2-phenyl-1-(1H-tetrazol-5-yl)ethan-1-ol; 2-azido-2-(naphthalen-2-yl)-1-(1H-tetrazol-5-yl)ethan-1-ol; 2-azido-2-(4-chlorophenyl)-1-(1H-tetrazol-5-yl)ethan-1-ol; 2-azido-1-(1H-tetrazol-5-yl)-2-(thiophen-2-yl)ethan-1-ol; 2-azido-4-phenyl-1-(1H-tetrazol-5-yl)but-3-en-1-ol; 2-azido-1-(1H-tetrazol-5-yl)nonan-1-ol; 2-azido-2-ethyl-1-(1H-tetrazol-5-yl)butan-1-ol; 2-azido-2,2-diphenyl-1-(1H-tetrazol-5-yl)ethan-1-ol; (1-azidocyclopentyl) (1H-tetrazol-5-yl)methanol; (1-azidocyclohexyl) (1H-tetrazol-5-yl)methanol; (1-azidocycloheptyl) (1H-tetrazol-5-yl)methanol; (1-azidocyclooctyl) (1H-tetrazol-5-yl)methanol; and (9-azido-9H-fluoren-9-yl) (1H-tetrazol-5-yl)methanol.

9. A process for manufacturing the compound of formula (I) according to claim 1, the method comprising:
starting from an epoxynitrile of formula (II):

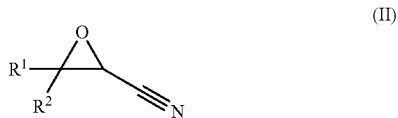

and performing the following steps:
(a) reacting the compound of formula (II) with an azide in presence of an organometallic catalyst, and
(b) performing a hydrolysis reaction to afford compound (I).

10. The process of claim 9, wherein the azide is trimethylsilyl azide.

11. The process of claim 9, wherein the organometallic catalyst is dibutyltin oxide.

12. The process of claim 9, wherein step (a) is executed in a solvent, said solvent being toluene.

13. The process of claim 9, wherein step (a) is executed at 60° C. for 18 h.

14. The process of claim 9, wherein the hydrolysis of step (b) is acidic hydrolysis.

15. An alpha-hydroxy-beta-triazole-tetrazole compound of formula (III):

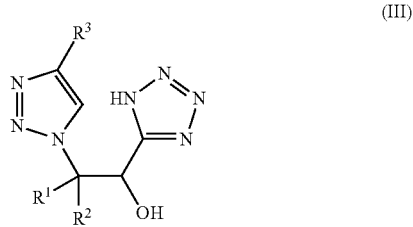

wherein $R^1$ and $R^2$ are each independently selected from the group consisting of hydrogen, hydrocarbyl, aryl, heteroaryl, hydrocarbylaryl, arylhydrocarbyl, hydrocarbylheteroaryl, or heteroarylhydrocarbyl groups; or $R^1$ and $R^2$ form together a hydrocarbyl, aryl, heteroaryl, hydrocarbylaryl, arylhydrocarbyl, hydrocarbylheteroaryl, or heteroarylhydrocarbyl groups;

wherein the group is optionally substituted by at least one hydrocarbyl, aryl, heteroaryl, oxo, hydroxyl, amido, amino, nitro, carboxylo, formyl, halo, thioxo or sulfhydryl;

wherein the group is optionally interrupted or terminated by at least one of —O—, —S—, or —NR$^N$—, wherein R$^N$ is selected from the group consisting of hydrogen, hydrocarbyl, aryl, and a combination thereof, and wherein the nitrogen and/or sulfur atoms are optionally oxidized; and wherein $R^3$ is hydrogen, an organic group or an organic molecule;

or a stereoisomer, salt or solvent thereof.

16. The compound according to claim 15, wherein $R^3$ is hydrogen, hydroxyl, amido, amino, cyano, tetrazolyl, triazolyl, nitro, borono, carboxylo, formyl, halo, haloformyl, phosphono, phosphate or sulfhydryl.

17. The compound according to claim 15, wherein $R^3$ is hydrogen, hydrocarbyl, aryl, heteroaryl, hydrocarbylaryl, arylhydrocarbyl, hydrocarbylheteroaryl, or heteroarylhydrocarbyl;

wherein the group is optionally substituted by at least one group being hydrocarbyl, aryl, heteroaryl, oxo, hydroxyl, amido, amino, cyano, tetrazolyl, triazolyl, nitro, carboxylo, formyl, halo, thioxo or sulfhydryl;

wherein the group is optionally interrupted or terminated by at least one of —O—, —S—, or —NR$^N$—, wherein R$^N$ is selected from the group consisting of hydrogen, hydrocarbyl, aryl, and a combination thereof, and wherein the nitrogen and/or sulfur atoms are optionally oxidized.

18. The compound according to claim 15, wherein $R^3$ is a carbohydrate, an amino acid, a peptide or a nucleoside.

19. The compound according to claim 15, wherein $R^3$ is selected from the group consisting of alkyl, alkenyl, aryl, heteroaryl, alkylaryl, arylalkyl, alkenylaryl, arylalkenyl, alkylheteroaryl, and heteroarylalkyl groups;

wherein the group is optionally substituted by at least one alkyl, alkenyl, aryl, heteroaryl, alkylaryl, arylalkyl, oxo, hydroxyl, amido, amino, tetrazolyl, triazolyl, nitro, carboxylo, formyl, halo, thioxo or sulfhydryl; and wherein the group is optionally interrupted or terminated by at least one of —O—, —S—, or —NR$^N$—, wherein R$^N$ is selected from the group consisting of hydrogen, alkyl, alkenyl, aryl, and a combination thereof.

20. The compound according to claim 15, selected from the group consisting of: (1-(4-phenyl-1H-1,2,3-triazol-1-yl)cyclohexyl) (1H-tetrazol-5-yl)methanol; (1-(4-phenyl-1H-1,2,3-triazol-1-yl)cycloheptyl) (1H-tetrazol-5-yl)methanol; (1-(4-phenyl-1H-1,2,3-triazol-1-yl)cyclooctyl) (1H-tetrazol-5-yl)methanol; tert-butyl 1-(1-(hydroxy(1H-tetrazol-5-yl)methyl)cyclooctyl)-1H-1,2,3-triazole-4-carboxylate; (1-(4-(3-chloropropyl)-1H-1,2,3-triazol-1-yl)cyclooctyl) (1H-tetrazol-5-yl)methanol; 2-(1-(1-(hydroxy(1H-tetrazol-5-yl)methyl)cyclooctyl)-1H-1,2,3-triazol-4-yl)ethan-1-ol; 2-ethyl-2-(4-phenyl-1H-1,2,3-triazol-1-yl)-1-(1H-tetrazol-5-yl)butan-1-ol; 2-(4-hexyl-1H-1,2,3-triazol-1-yl)-2-phenyl-1-(1H-tetrazol-5-yl)ethan-1-ol; 2-(4-hexyl-1H-1,2,3-triazol-1-yl)-2,2-diphenyl-1-(1H-tetrazol-5-yl)ethan-1-ol; 2-(4-(3-chloropropyl)-1H-1,2,3-triazol-1-yl)-2,2-diphenyl-1-(1H-tetrazol-5-yl)ethan-1-ol; and tert-butyl 1-(2-hydroxy-1,1-diphenyl-2-(1H-tetrazol-5-yl)ethyl)-1H-1,2,3-triazole-4-carboxylate.

* * * * *